(12) United States Patent
van der Burg et al.

(10) Patent No.: US 8,821,495 B2
(45) Date of Patent: Sep. 2, 2014

(54) SYSTEM AND METHOD FOR HYOIDPLASTY

(75) Inventors: Erik J. van der Burg, Los Gatos, CA (US); Michael T. Dineen, San Francisco, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1692 days.

(21) Appl. No.: 10/736,457

(22) Filed: Dec. 15, 2003

(65) Prior Publication Data

US 2005/0126563 A1 Jun. 16, 2005

(51) Int. Cl.
*A61F 2/46* (2006.01)
*A61F 2/20* (2006.01)

(52) U.S. Cl.
USPC .................................. 606/86 R; 623/9

(58) Field of Classification Search
USPC .......... 606/71, 282, 151, 324; 254/13, 17, 92, 254/119, 124, 126, 104, 231; 108/6; 269/34, 43, 104, 237, 216–218; 24/274 P, 489, 502, 503, 514–517, 525, 24/568, 569; 600/219, 225, 237, 243–245; 248/228.4, 230.4, 231.51, 316.2, 248/316.5; 294/193, 195, 198; 623/9; 33/27.02
See application file for complete search history.

(56) References Cited

U.S. PATENT DOCUMENTS

| | | | | |
|---|---|---|---|---|
| 19,589 A * | 3/1858 | Schafer | .......................... | 33/27.02 |
| 119,875 A * | 10/1871 | Nichols | .......................... | 33/27.02 |
| 298,568 A * | 5/1884 | Fisher | .......................... | 254/126 |
| 466,016 A * | 12/1891 | Gustin et al. | .................... | 403/18 |
| 682,294 A * | 9/1901 | Terlin | .......................... | 33/27.02 |
| 879,547 A * | 2/1908 | Holter | .......................... | 269/54.2 |
| 1,279,537 A * | 9/1918 | Grube | .......................... | 33/27.02 |
| 1,569,275 A * | 1/1926 | Green | .......................... | 269/130 |
| 1,871,713 A * | 8/1932 | Lowenthal | .................... | 269/54.3 |
| 2,297,999 A * | 10/1942 | Eubanks | ....................... | 33/27.02 |
| 2,433,760 A * | 12/1947 | Janes | .......................... | 269/130 |
| 2,674,966 A * | 4/1954 | Morris | .......................... | 269/201 |
| 2,966,907 A * | 1/1961 | Fasolino | ........................ | 606/74 |
| 3,488,779 A * | 1/1970 | Christensen | .............. | 623/16.11 |
| 3,862,631 A * | 1/1975 | Austin | .......................... | 606/60 |
| 3,944,202 A * | 3/1976 | Dearman | ...................... | 269/130 |
| 4,156,313 A * | 5/1979 | Lied | .............................. | 33/27.02 |
| 4,236,703 A * | 12/1980 | Stevenson | ....................... | 269/41 |
| 4,317,451 A * | 3/1982 | Cerwin et al. | ................. | 606/220 |
| 4,445,513 A * | 5/1984 | Ulrich et al. | ................ | 606/86 A |
| 4,623,085 A * | 11/1986 | Dearman | ..................... | 228/49.3 |
| 4,666,138 A * | 5/1987 | Dearman | ........................ | 269/43 |
| 4,723,540 A * | 2/1988 | Gilmer, Jr. | ..................... | 606/75 |
| 4,741,698 A * | 5/1988 | Andrews | ....................... | 433/173 |

(Continued)

OTHER PUBLICATIONS

Timothy J. Patton, M.D., Joseph H. Ogura, M.D. and Stanley E. Thawley, M.D., "Expansion Hyoidplasty," 1983 First-Place Resident Research Award: Clinical Category, vol. 92, No. 5, Oct. 1984.

(Continued)

*Primary Examiner* — David Bates

(57) ABSTRACT

Methods and devices are disclosed for manipulating the hyoid bone, such as to treat obstructive sleep apnea. An implant is positioned adjacent a hyoid bone. The spatial orientation of the hyoid bone is manipulated, to affect the configuration of the airway. The implant restrains the hyoid bone in the manipulated configuration. The implant is positioned adjacent to pharyngeal structures to dilate the pharyngeal airway and/or to support the pharyngeal wall against collapse.

12 Claims, 32 Drawing Sheets

(56) References Cited

U.S. PATENT DOCUMENTS

| | | | |
|---|---|---|---|
| 5,176,618 A | 1/1993 | Freedman | |
| 5,693,100 A * | 12/1997 | Pisharodi | 623/17.16 |
| 5,979,456 A | 11/1999 | Magovern | |
| 5,988,171 A | 11/1999 | Sohn et al. | |
| 6,161,541 A * | 12/2000 | Woodson | 128/848 |
| 6,176,479 B1 * | 1/2001 | Hicklin | 269/156 |
| 6,267,589 B1 * | 7/2001 | Farzin-Nia et al. | 433/7 |
| 6,328,753 B1 | 12/2001 | Zammit | |
| 6,355,036 B1 * | 3/2002 | Nakajima | 606/57 |
| 6,408,851 B1 | 6/2002 | Karell | |
| 6,440,145 B1 * | 8/2002 | Assawah | 606/151 |
| 6,536,439 B1 | 3/2003 | Palmisano | |
| 6,634,362 B2 | 10/2003 | Conrad et al. | |
| 6,685,742 B1 * | 2/2004 | Jackson | 623/17.11 |
| 7,189,237 B2 * | 3/2007 | Huebner | 606/291 |
| 7,588,579 B2 * | 9/2009 | Mommaerts | 606/105 |
| 2003/0149445 A1 | 8/2003 | Knudson et al. | |
| 2003/0149488 A1 | 8/2003 | Metzger et al. | |
| 2004/0102776 A1 * | 5/2004 | Huebner | 606/69 |
| 2004/0102778 A1 * | 5/2004 | Huebner et al. | 606/71 |

OTHER PUBLICATIONS

Jay F. Piccirillo and Stanley E. Thawley, "Sleep-Disordered Breathing," Cummings: Otolaryngology: Head and Neck Surgery, $3^{rd}$ ed., Copyright © 1998 Mosby-Year Book, Inc., Chapter 81, pp. 1546-1571.

Anil N. Rama, M.D., MPH, Shivan H. Tekwani, BS and Clete A. Kushida, M.D., Ph.D., "Sites of Obstruction in Obstructive Sleep Apenea," www.chestjournal.org, Oct. 2002.

* cited by examiner

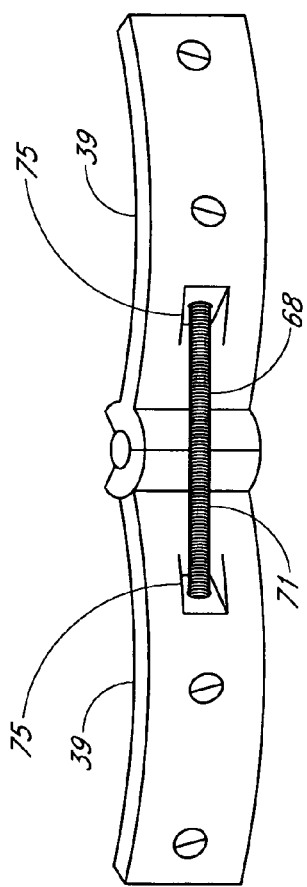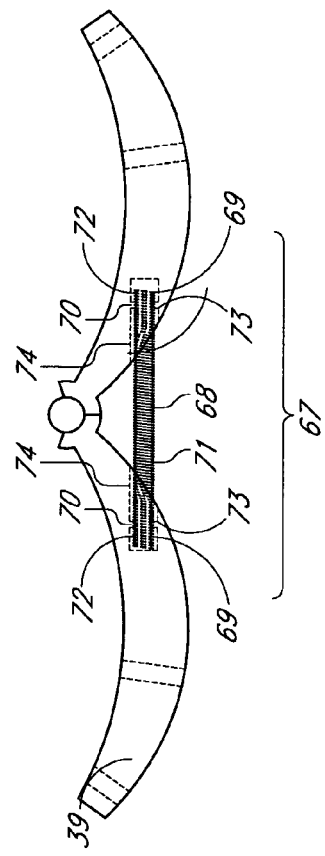

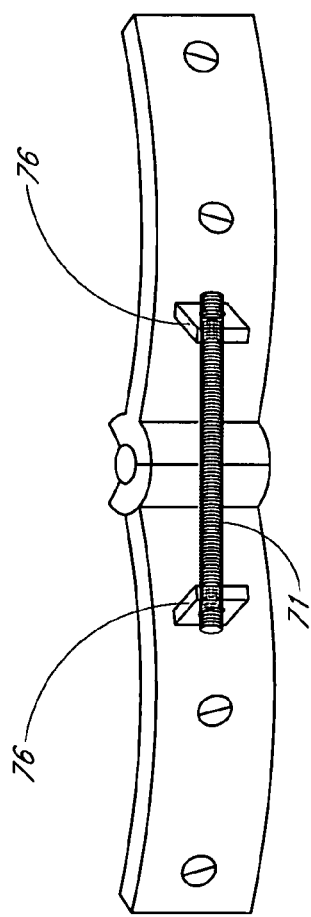
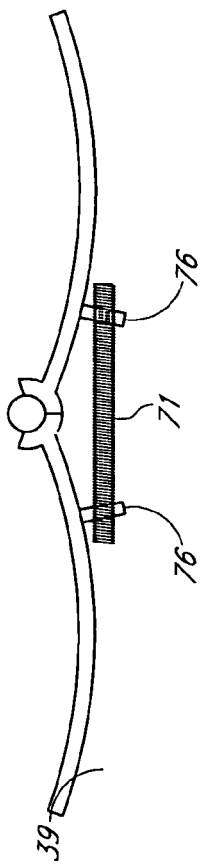
FIG. 14A
FIG. 14B

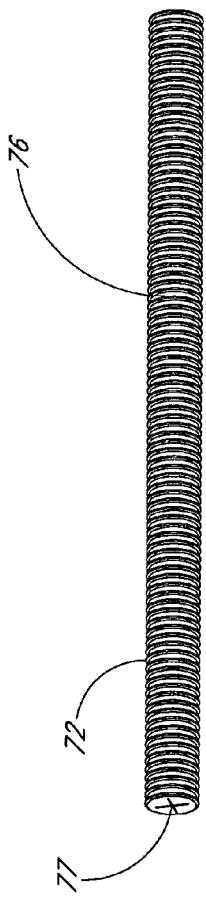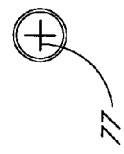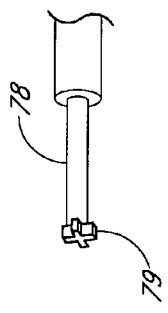
FIG. 15A
FIG. 15B
FIG. 15C

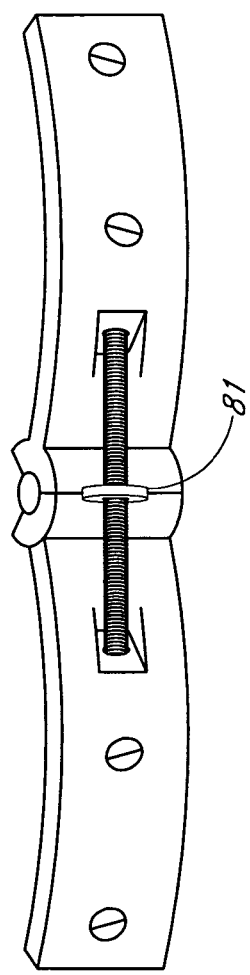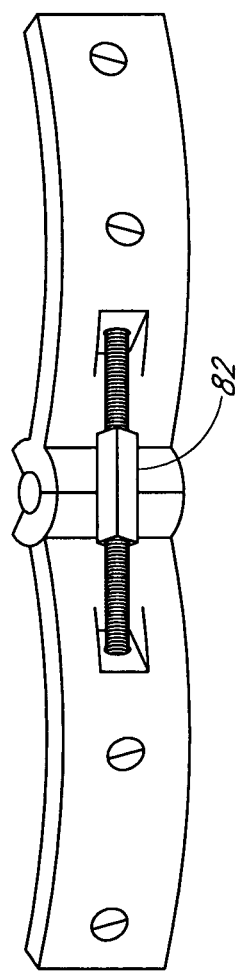

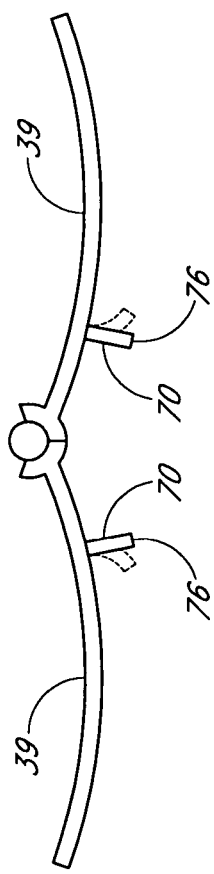
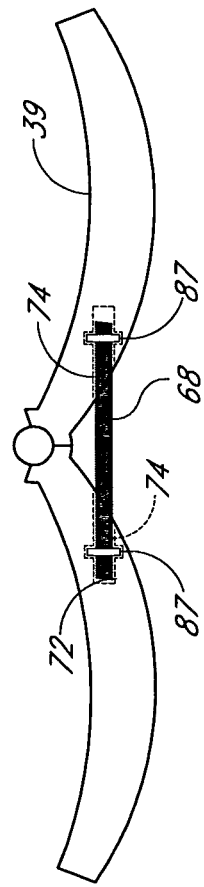
FIG. 19A
FIG. 19B

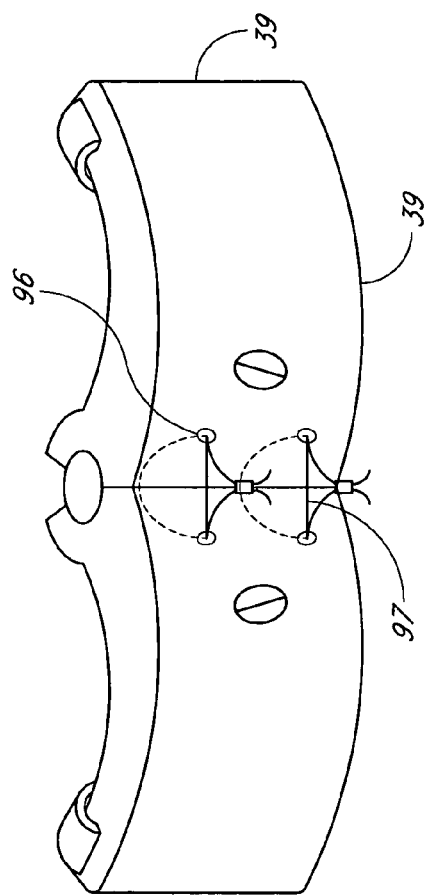
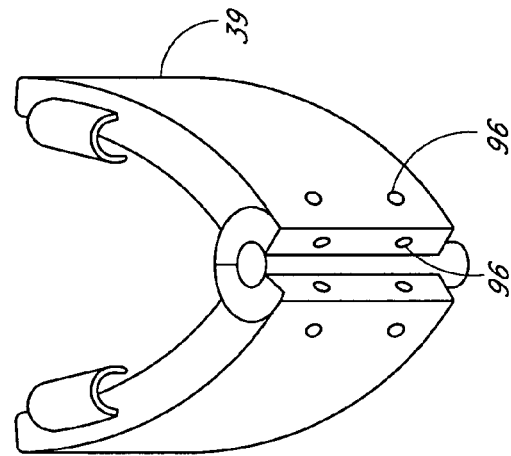
FIG. 21A
FIG. 21B

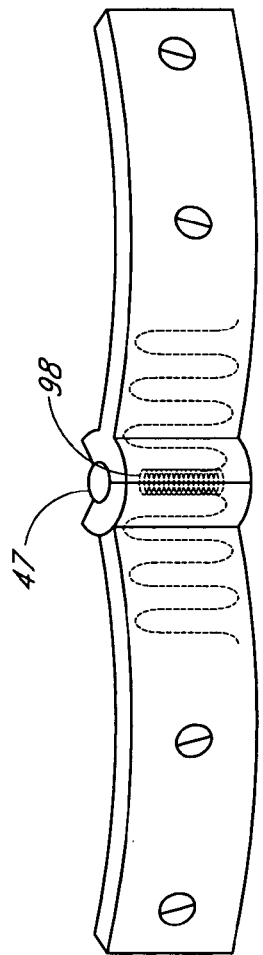
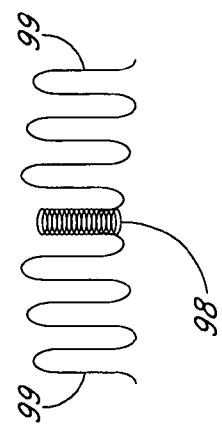
FIG. 22A
FIG. 22B

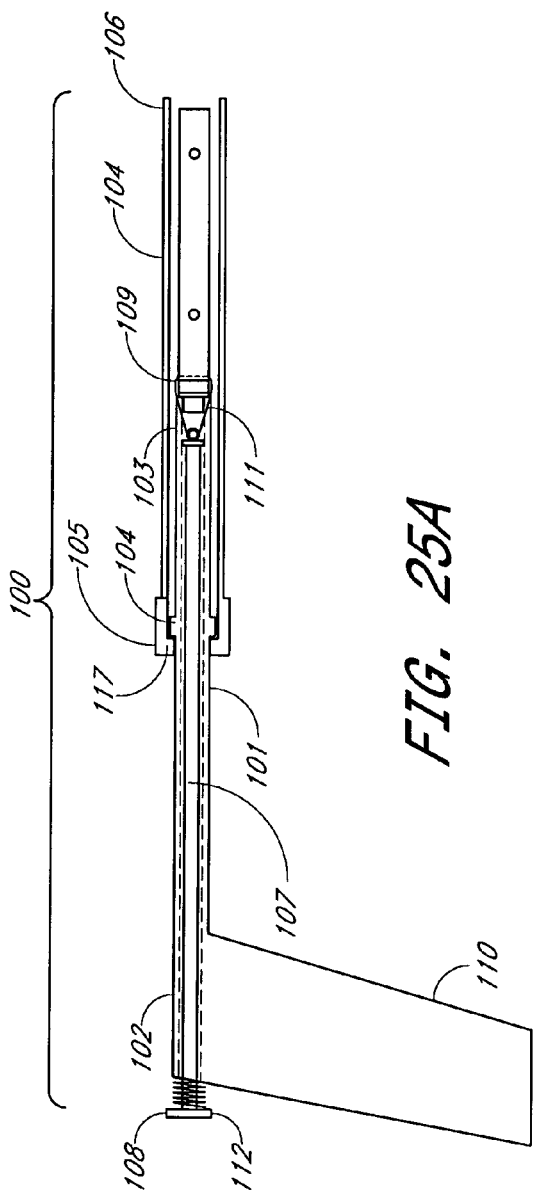
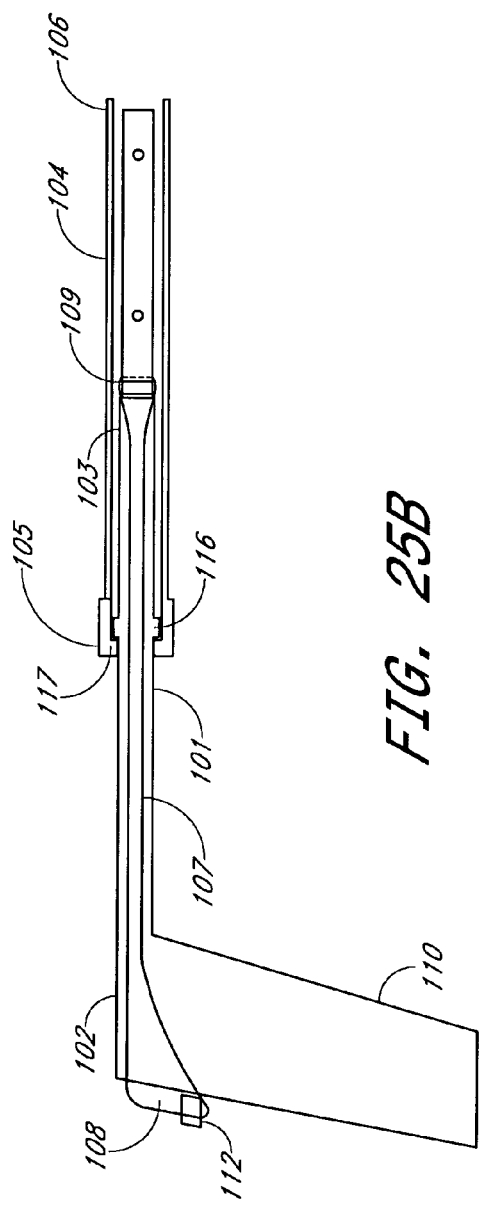
FIG. 25A
FIG. 25B

SYSTEM AND METHOD FOR HYOIDPLASTY

BACKGROUND OF THE INVENTION

1. Field of the Invention

This invention relates generally to a system and method for treating upper airway obstruction, sleep disordered breathing, upper airway resistance syndrome and snoring.

2. Description of the Related Art

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per night.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn can causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather an narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias and measurement of nasal or oral airflow and pulse oximetry to measure to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices are low for several reasons. Sleeping with a sealed nasal mask is uncomfortable for patients. Smaller sealed nasal masks may be more comfortable to patients but are ineffective is patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause regurgitation of food and liquids into the nasopharynx.

Laser-assisted uvulopalatopharyngoplasty (LAUP) is a similar procedure to UPPP that uses a CO2 laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment of the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone is typically a single bone or cartilage.

Notwithstanding the foregoing, there remains a need for improved methods and devices for treating obstructive sleep apnea.

SUMMARY OF THE INVENTION

There is provided in accordance with one aspect of the present invention, a method of performing hyoidplasty. The method comprises the steps of accessing a hyoid bone, having a first and a second greater horn spaced apart by a first distance. The space between the first and second greater horns is increased to a second distance, and the first and second greater horns are restrained at the second distance. The hyoid bone accessed may be a human hyoid bone.

In one implementation of the invention, the accessing step is accomplished in a minimally invasive procedure.

The increasing the space step may comprise flexing the hyoid bone, separating the hyoid bone into at least two components, or separating the hyoid bone into at least three components. The second distance may be at least about 110%, in some procedures at least about 120% and in other procedures at least about 130% of the first distance. The restraining step may comprise securing the hyoid bone to a hyoid bone support. Alternatively, the restraining step may occur without attaching an implant to the hyoid bone.

In accordance with another aspect of the present invention, there is provided an implant for attachment to a hyoid bone. The implant comprises an implant body, having a first attachment zone configured for attachment to a first portion of a hyoid bone. The implant body includes a second attachment zone, configured for attachment to a second portion of a hyoid bone. A connection is provided between the first and second attachment zones, which allows movement of the first and second attachment zones with respect to each other. A lock may be carried by the body, for fixing the relationship between the first and second attachment zones.

The connection may comprise a flexible portion of the body. Alternatively, the connection may comprise a hinge, pivot or a flexible element carried by the body. The lock may comprise a threaded shaft, or any of a variety of interference fit structures.

In accordance with a further aspect of the present invention, there is provided a method of treating a patient. The method comprises the steps of providing a hyoid bone support, having a first arm and a second arm which are transformable from a moveable relationship with respect to each other to a fixed relationship with respect to each other. The first arm is attached to a first part of a hyoid bone. The second arm is attached to a second part of a hyoid bone. The configuration of the hyoid bone is changed, and the support is secured in the fixed relationship.

The changing the configuration step may comprise increasing a lateral distance between the first and second parts of the hyoid bone, and/or increasing an anterior-posterior distance between the first and second parts of the hyoid bone. Increasing the anterior-posterior distance may comprise the insertion of at least one spacer between the first and second parts, and/or attaching a brace to the first and second arms of the hyoid bone support to expand the distance between the first arm and the second arms. The changing the configuration step may be accomplished either before or after the attaching steps.

In one implementation of the invention, the attaching step comprises attaching the first and second arms to the hyoid bone using screws. Alternatively, the attaching step may comprise using one or more bone clips, sutures, adhesives, or other attachment techniques known in the art.

The hyoid bone also comprises an arc length along the bone, between the ends of the first and second greater horns. Any of the foregoing methods may additionally comprise the step of increasing the arc length of the hyoid bone, such as by separating the hyoid bone into two or more component parts and providing a space between the adjacent parts. The bone components may then be secured with respect to each other.

In accordance with a another embodiment of the present invention, there is provided a method of treating a patient. The method comprises identifying the hyoid bone, having a first and second greater horns and a midpoint on the hyoid bone halfway between the ends of the first and second greater horns such that a first line extending from the midpoint through an end of the first greater horn and a second line extending from the midpoint through an end of the second greater horn define an angle. The angle is changed and the hyoid bone is secured to retain the changed angle. Access to the hyoid bone may be accomplished in a minimally invasive procedure.

In accordance with another embodiment of the invention, there is provided still another method for treating a patient. The method comprises the steps of providing a pharyngeal support, having a first arm and a second arm which are transformable from a moveable relationship with respect to each other to a fixed relationship with respect to each other. The first arm is positioned with respect to a first part of the pharynx and the second part is positioned with respect to another part of the pharynx. The configuration of the pharynx is changed and the support is secured in the fixed relationship.

The positioning step may comprise forming an interference fit in a fascial plane in proximity to a pharyngeal wall or between two pharyngeal muscles. The pharyngeal muscles may be a suprahyoid muscle and/or an infrahyoid muscle.

In one implementation of the invention, the method further comprises attaching at least one arm of the pharyngeal support to a part of the pharynx. The attaching step may be performed using a tissue anchor, hook, suture, clip or adhesive. The attaching step may occur before or after the changing the configuration step.

There is provided in accordance with another aspect of the present invention an implant for positioning in a pharyngeal structure, comprising an implant body; a first tissue contact zone configured for contacting a first portion of a pharyngeal structure, a second tissue contact zone configured for contacting a second portion of a pharyngeal structure, a connection between the first and second contact zones which allows movement of the first and second contact zones with respect to each other and a lock carried by the body for fixing the relationship between the first and second contact zones. The portion of a pharyngeal structure may comprise a suprahyoid muscle, an infrahyoid muscle or a hyoid bone.

Further features and advantages of the present invention will become apparent to those of skill in the art in view of the disclosure herein, when considered together with the attached drawings and claims.

BRIEF DESCRIPTION OF THE DRAWINGS

The structure and method of using the invention will be better understood with the following detailed description of embodiments of the invention, along with the accompanying illustrations, in which:

FIGS. 13A and 13B are anterior and superior views of one embodiment of the configuration lock of the hyoid brace where the locking interface is embedded within the hyoid brace.

FIGS. 14A and 14B are anterior and superior views of another embodiment of the configuration lock of the hyoid brace where the configuration locking interface protrudes from the hyoid brace.

FIGS. 15A and 15B are lateral and end views of one embodiment of the invention with a locking member having a rotational interface. FIG. 15C shows the tool that inserts into the rotational interface.

FIGS. 16A and 16B depict embodiments of the invention with a grippable surface on the locking member.

FIGS. 19A and 19B depict embodiments of the invention with tiltable locking interfaces.

FIGS. 21A and 21B illustrate one embodiment of configuration lock utilizing suture knots.

FIGS. 22A and 22B represent one embodiment of invention using a tension spring.

FIGS. 25A and 25B are some embodiments of a delivery tool capable of minimally invasive insertion.

DETAILED DESCRIPTION OF THE PREFERRED EMBODIMENT

A. Anatomy of the Pharynx

Figure 1:
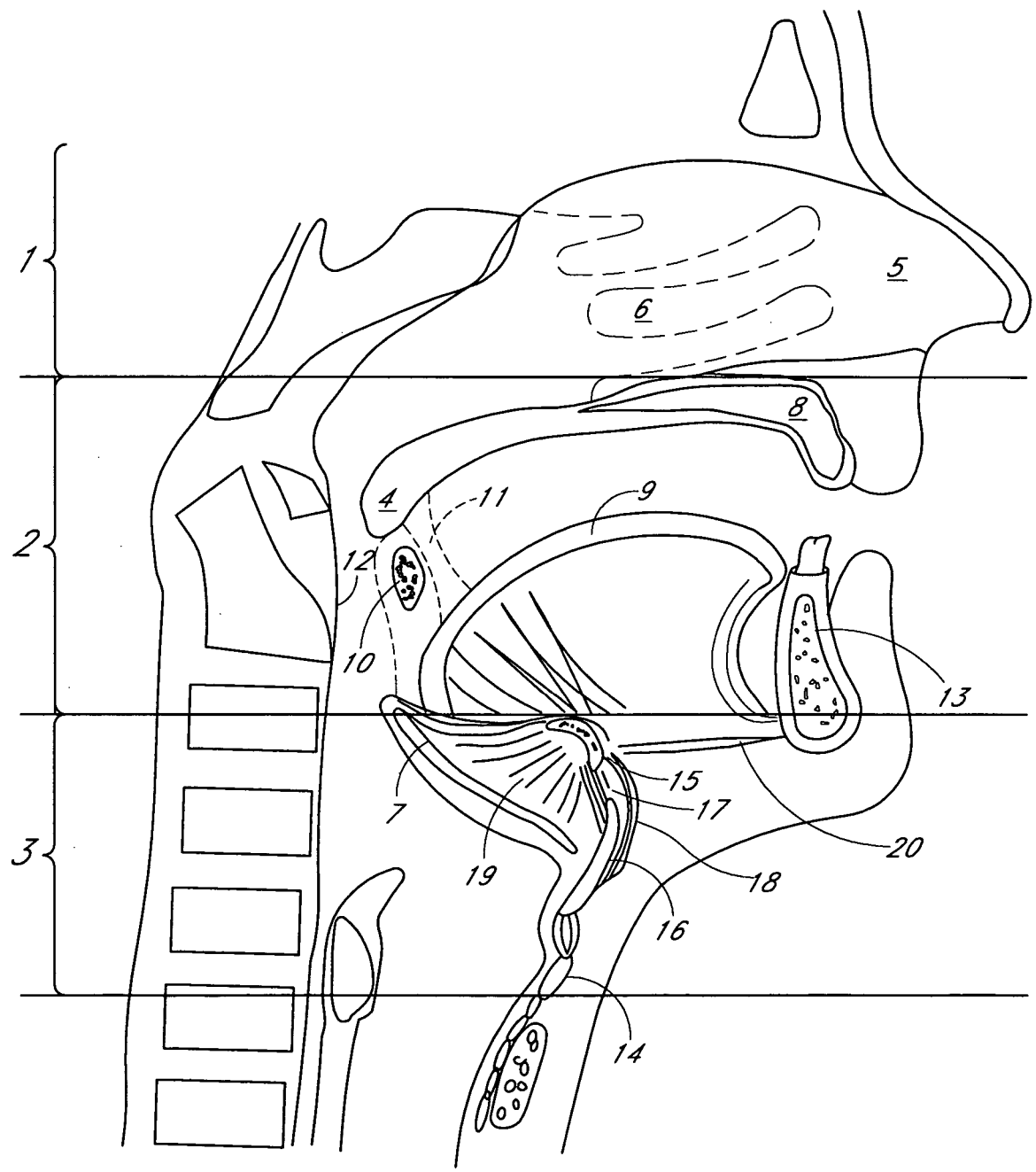
FIG. 1 is a sagittal view of the pharynx.

FIG. 1 is a sagittal view of the structures that comprise the pharyngeal airway and may be involved in obstructive sleep apnea. The pharynx is divided, from superior to inferior, into the nasopharynx 1, the oropharynx 2 and the hypopharynx 3. The nasopharynx 1 is less common source of obstruction in OSA. The nasopharynx is the portion of the pharynx above the soft palate 4. In the nasopharynx, a deviated nasal septum 5 or enlarged nasal turbinates 6 may occasionally contribute to upper airway resistance or blockage. Only rarely, a nasal mass, such as a polyp, cyst or tumor may be a source of obstruction.

The oropharynx 2 comprises structures from the soft palate 4 to the upper border of the epiglottis 7 and includes the hard palate 8, tongue 9, tonsils 10, palatoglossal arch 11, the posterior pharyngeal wall 12 and the mandible 13. An obstruction in the oropharynx 2 may result when the tongue 9 is displaced posteriorly during sleep as a consequence of reduced muscle activity during REM sleep. The displaced tongue 9 may push the soft palate 4 posteriorly and may seal off the nasopharynx 1 from the oropharynx 2. The tongue 9 may also contact the posterior pharyngeal wall 12, which causes further airway obstruction.

The hypopharynx 3 comprises the region from the upper border of the epiglottis 7 to the inferior border of the cricoid cartilage 14. The hypopharynx 3 further comprises the hyoid bone 15, a U-shaped, free floating bone that does not articulate with any other bone. The hyoid bone 15 is attached to surrounding structures by various muscles and connective tissues. The hyoid bone 15 lies inferior to the tongue 9 and superior to the thyroid cartilage 16. A thyrohyoid membrane 17 and a thyrohyoid muscle 18 attaches to the inferior border of the hyoid 15 and the superior border of the thyroid cartilage 16. The epiglottis 7 is infero-posterior to the hyoid bone 15 and attaches to the hyoid bone by a median hyoepiglottic ligament 19. The hyoid bone attaches anteriorly to the inferoposterior aspect of the mandible 13 by the geniohyoid muscle 20.

Figure 2C:
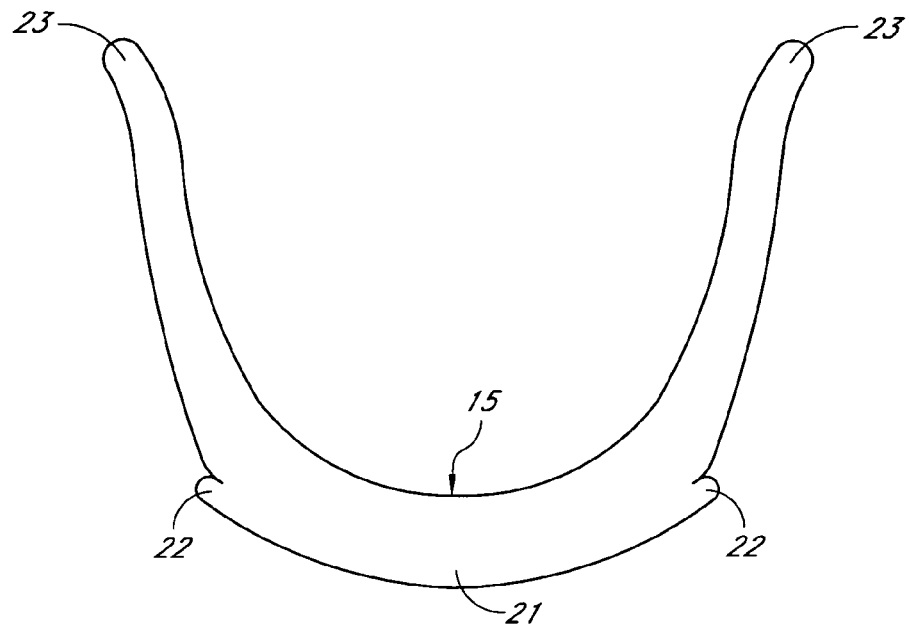
FIG. 2C is a superior view of the hyoid bone.
Figures 2A, 2B:
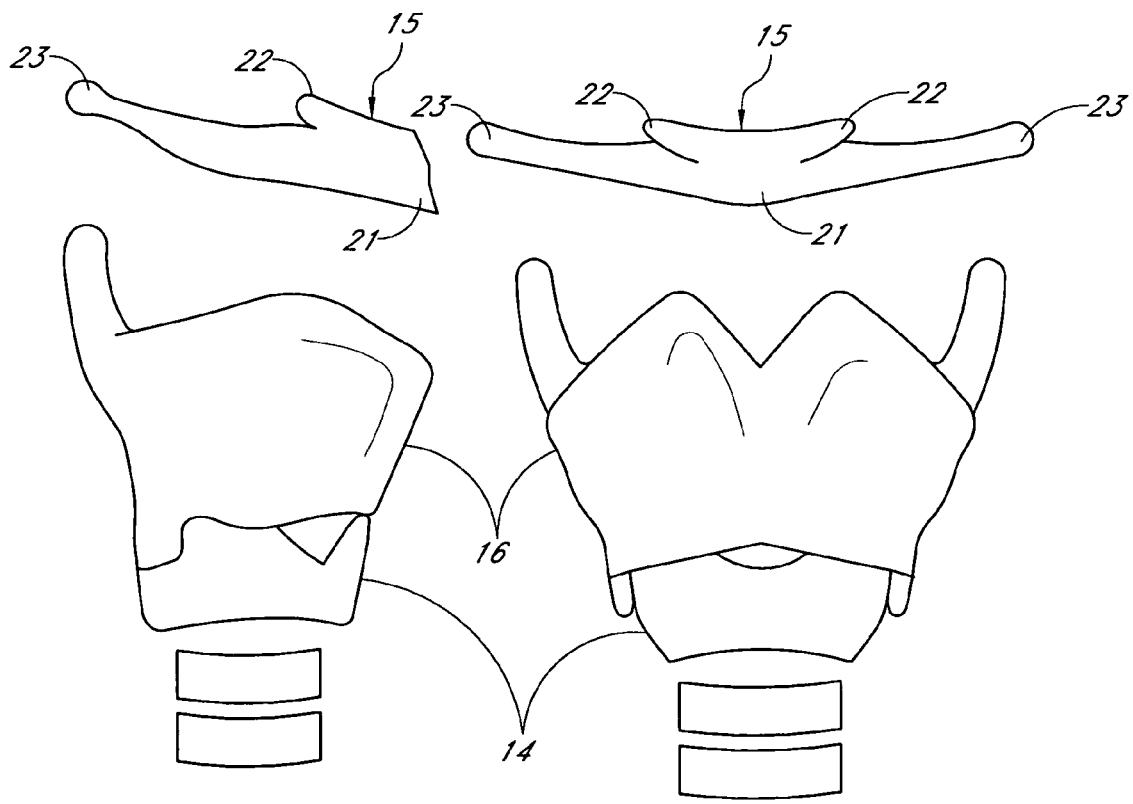
FIGS. 2A and 2B depict the hyoid bone with respect to the thyroid and cricoid cartilage in a lateral and anterior view, respectively.
Figure 3:
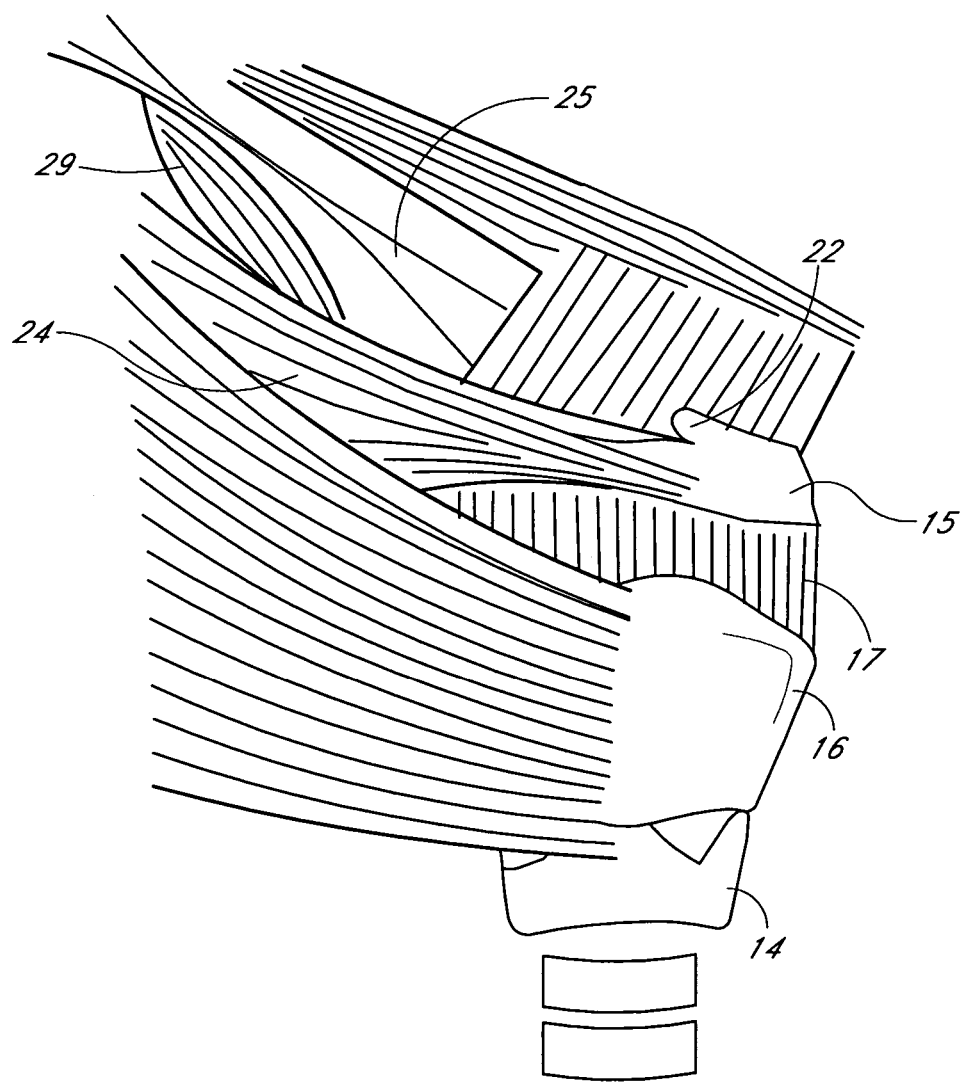
FIG. 3 illustrates the musculature attached to the hyoid bone in a lateral view.
Figure 4:
FIG. 4 shows an anterior view of the musculature attached to the hyoid bone. The right side depicts the superficial musculature and the left side shows the deep musculature.

The position of the hyoid bone relative to the thyroid and cricoid cartilage is shown in FIGS. 2A and 2B. The hyoid bone is a U-shaped bone comprising a body 21, two lesser horns 22 and two greater horns 23, as a shown in a superior view in FIG. 2C. As shown in FIG. 3, at the pharyngeal level of the hyoid bone, the hyoid bone forms an anterior portion of the pharynx while a pair of middle constrictor muscles 24 form the remaining portions of the airway. The muscle fibers of the middle constrictor muscles 24 originate from the greater 23 and lesser horns 22 of the hyoid bone 15 and fan out posteriorly, inferiorly and superiorly to the posterior midline pharynx (not shown). A stylohyoid ligament 25 attaches from the cranium to the hyoid bone. FIG. 4 illustrates the attachments of the extrinsic muscles of the larynx. The left side of the illustration in FIG. 4 depicts the anatomy of the superficial musculature and the right side depicts the deeper musculature. The posterior belly 26 of the digastric muscle originates from the mastoid process 27 and attaches to the lesser horn 22 of the hyoid bone 15 as a tendon and then attaches as an anterior belly 28 to the mandible 13. The stylohyoid muscle 29 originates from the styloid process (not shown) of the cranium and then splits into two portions upon inserting adjacent to the lesser horn of the hyoid bone 15 to allow the digastric muscle to pass anteriorly. Deep to the digastric 26, 28 and stylohyoid 29 muscles are the hyoglossus muscles 30, attaching to the superior surfaces of the greater horns 23 of the hyoid bone 15 and inserting into the lateral areas of the tongue 9. Further deep is the mylohyoid muscle 31, a sheet of muscle that courses between the hyoid bone 15 and the lateral interior sides of the mandible 13, forming a portion of the musculature of the floor of the mouth along with the geniohyoid muscle 20. These muscles move the hyoid bone 15 and tongue 9 superiorly and anteriorly, and are involved in the act of swallowing. Overlying most of the antero-lateral neck is the platysma muscle (not shown) that originates over the upper anterior chest and inserts over the anterior surfaces of the mandible 13.

The omohyoid muscles 32 are the most lateral of the muscles that attach to the inferior surface of the hyoid bone 15. The omohyoid muscles 32 also has two bellies. The inferior belly 33 attaches to the scapula and the superior belly 34 attaches to the inferior body of the hyoid bone. The two bellies 33, 34 are joined by a tendon 32 that is continuous with fascia along the medial ends of the clavicles 46. Also attached to the inferior surfaces of the hyoid bone are the sternohyoid muscles 35 that originate at the manubrium 36 of the sternum and the thyrohyoid 18 muscles that originate along anteroinferior border of the thyroid cartilage 16. The inferior muscles of the hyoid bone act to increase the luminal opening of the pharynx at the level of the hyoid.

B. Hyoid Brace

Figure 5A:
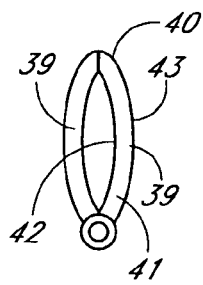
FIGS. 5A and 5B are superior and lateral views of one embodiment of the invention, with the hyoid brace in a folded position.
Figure 5B:
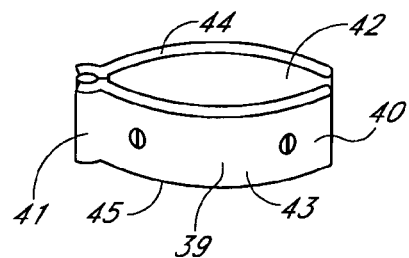
Figure 5C:
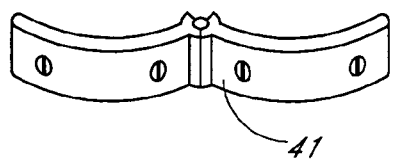
FIGS. 5C and 5D show the brace in an unfolded position.
Figure 5D:
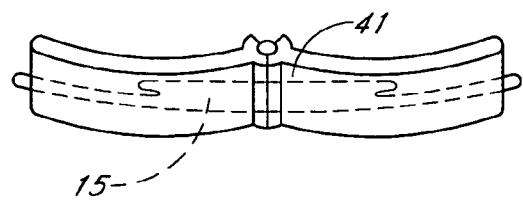

In one embodiment shown in FIGS. 5A and 5B, the hyoid brace or hyoidplasty implant comprises at least two brace arms 39, each with a lateral end 40, a medial end 41, an inner surface 42 capable of facing the hyoid bone or portion thereof, an outer surface 43, a superior surface 44 and an inferior surface 45. Hyoidplasty, as used herein, shall be given its ordinary meaning, and shall also include any alteration in the configuration or location of the hyoid bone or bone segments, including changes in angulation, anterior-posterior dimensions, lateral wall dimensions and/or removal of at least a portion of the hyoid bone. In one embodiment, the hyoid brace also has a flex point such as a pivot joint that joins the two brace arms 39. The pivot joint provides the hyoid brace with a folded position and a unfolded position. In the folded position, shown in FIG. 5B, the two lateral ends 40 of the hyoid brace are in closer proximity with one another. In the unfolded position, shown in FIG. 5C, the two lateral ends 40 are farther apart. FIG. 5D depicts the hyoid brace in proximity to the hyoid bone.

Figure 6A:
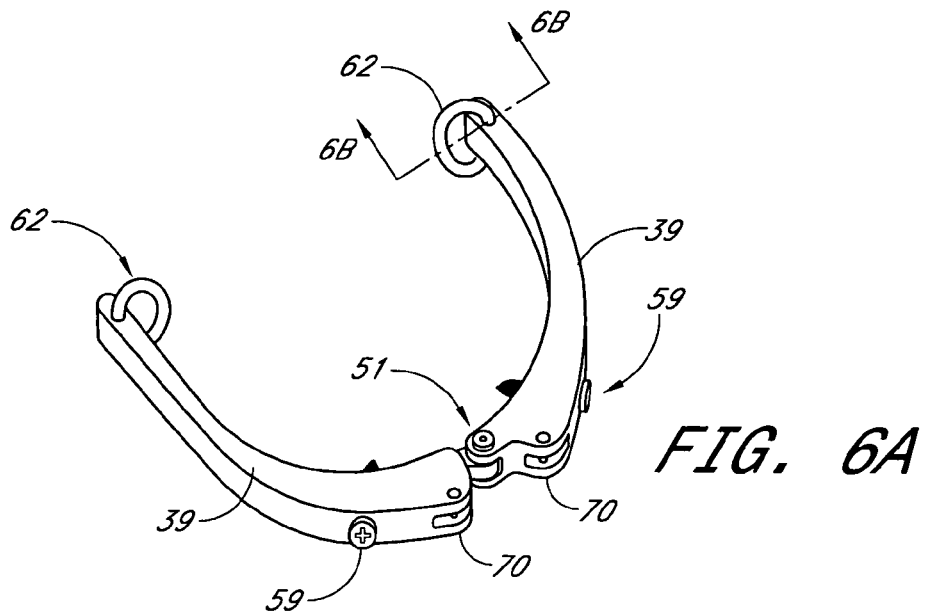
FIGS. 6A through 6C represent at least one embodiment of the invention, utilizing a clevis pin pivot joint and a combination of bone screws and hooks to attach the hyoid brace to the hyoid bone.
Figure 7A:
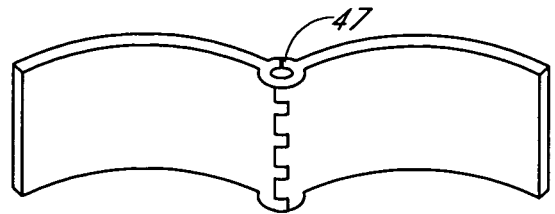
FIGS. 7A through 7D represent at least one embodiment of the invention, using various pivot joints.
Figure 7B:
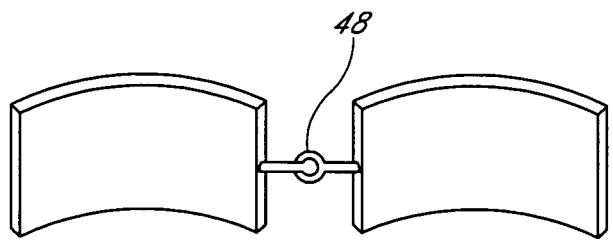
Figure 7C:
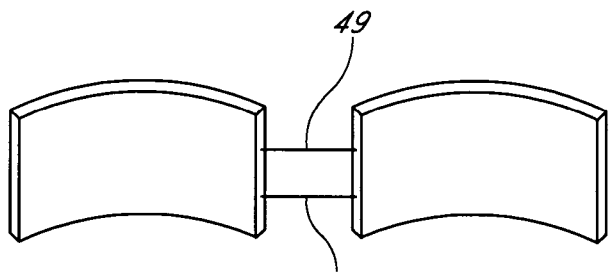
Figure 7D:
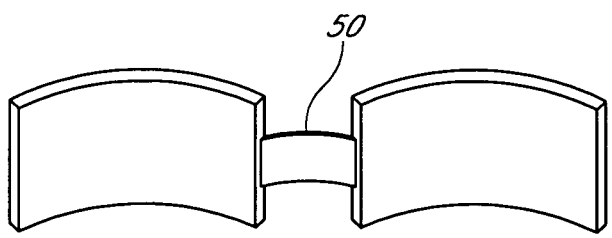

In one embodiment shown by FIG. 6A, the flex point comprises a clevis pin 51. In another embodiment, the flex point comprises a hinge joint 47, as in FIG. 7A. In a further embodiment, the hinge joint is limited to a particular range of movement. In one embodiment, shown in FIG. 7B, the pivot joint comprises a ball and socket joint 48. In another embodiment depicted in FIG. 7C, the pivot joint comprises one or more wires 49. In another embodiment, the wires resist axial loading. In another embodiment, the wires resist axial loading but are capable of limited flexion. In another embodiment, the pivot joint comprises one or more ribbons 50, as illustrated in FIG. 7D.

Figure 8A:
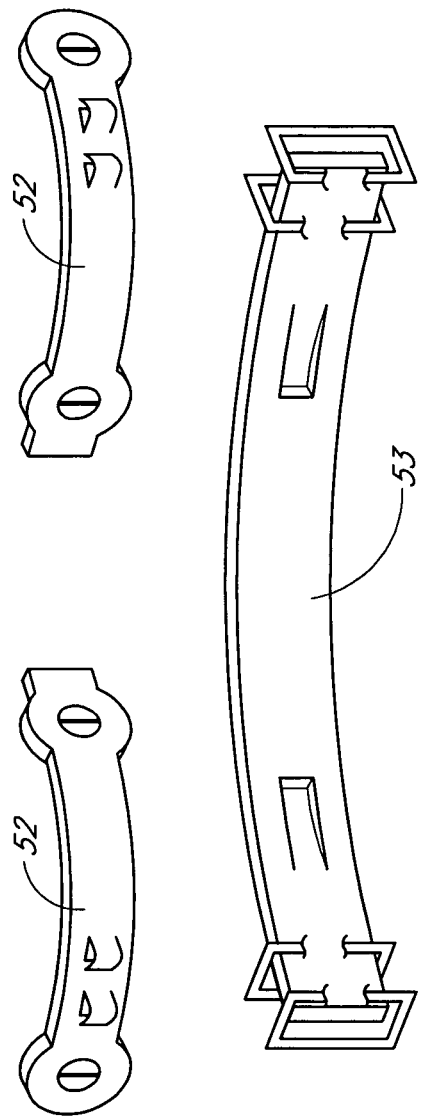
FIG. 8A depicts a system suitable for practicing at least one embodiment of the invention, comprising two brace arms and a bridge.
Figure 8B:
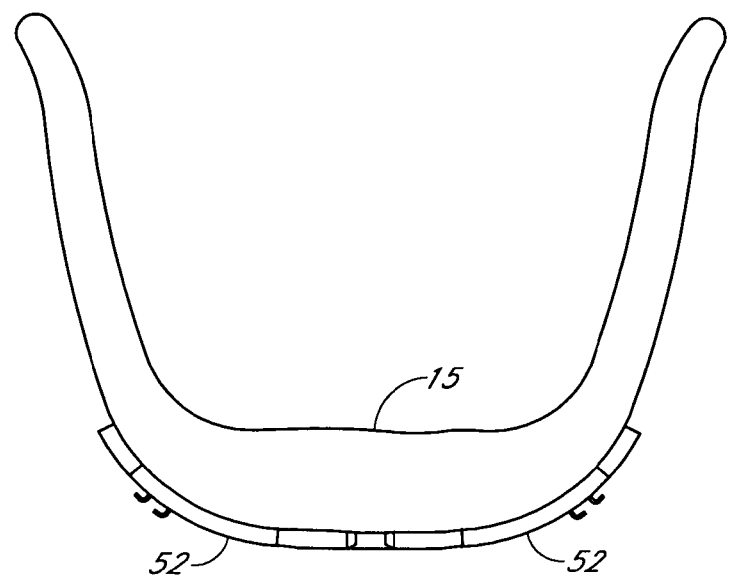
FIG. 8B shows the brace arms attached to a hyoid bone and FIG. 8C illustrates the attachment of the bridge.
Figure 8C:
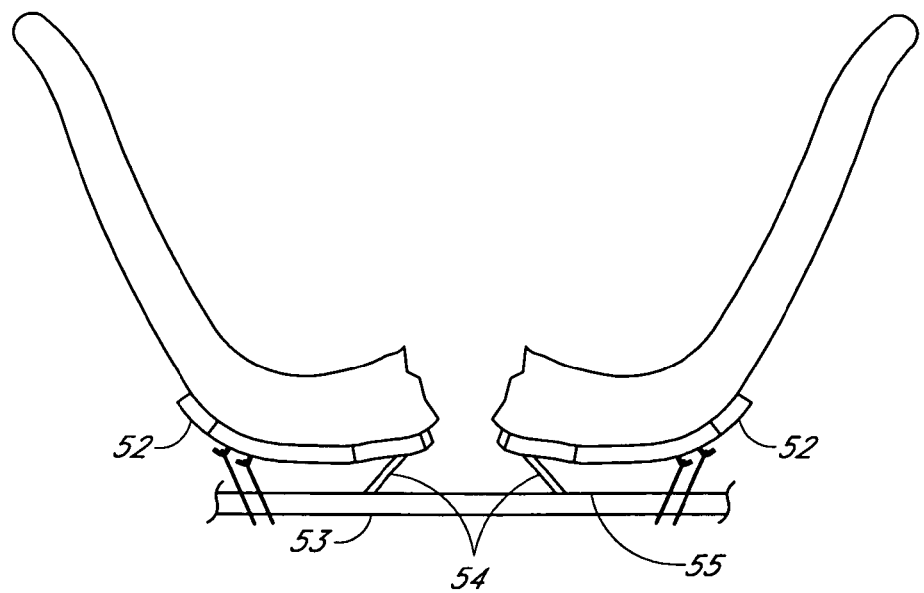
Figure 9:
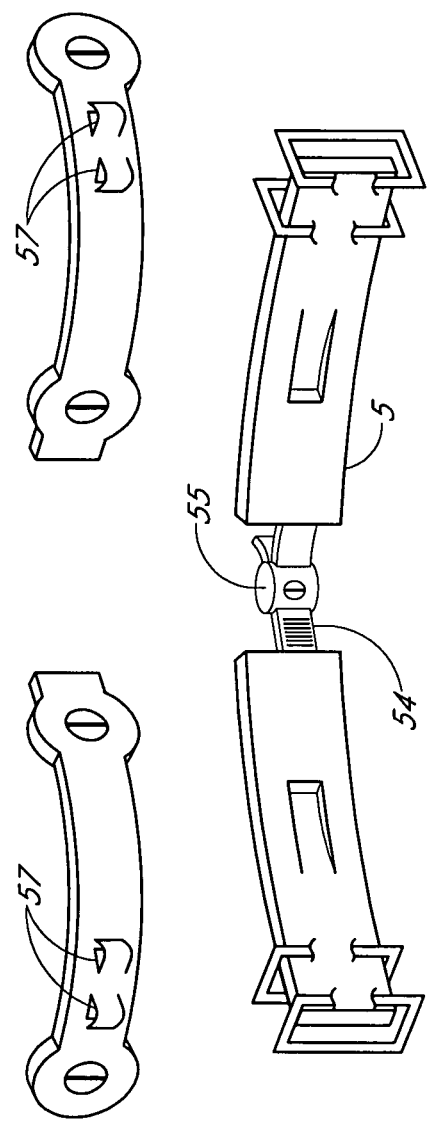
FIG. 9 depicts another embodiment of the invention with two brace arms and an adjustable width bridge.
Figure 10:
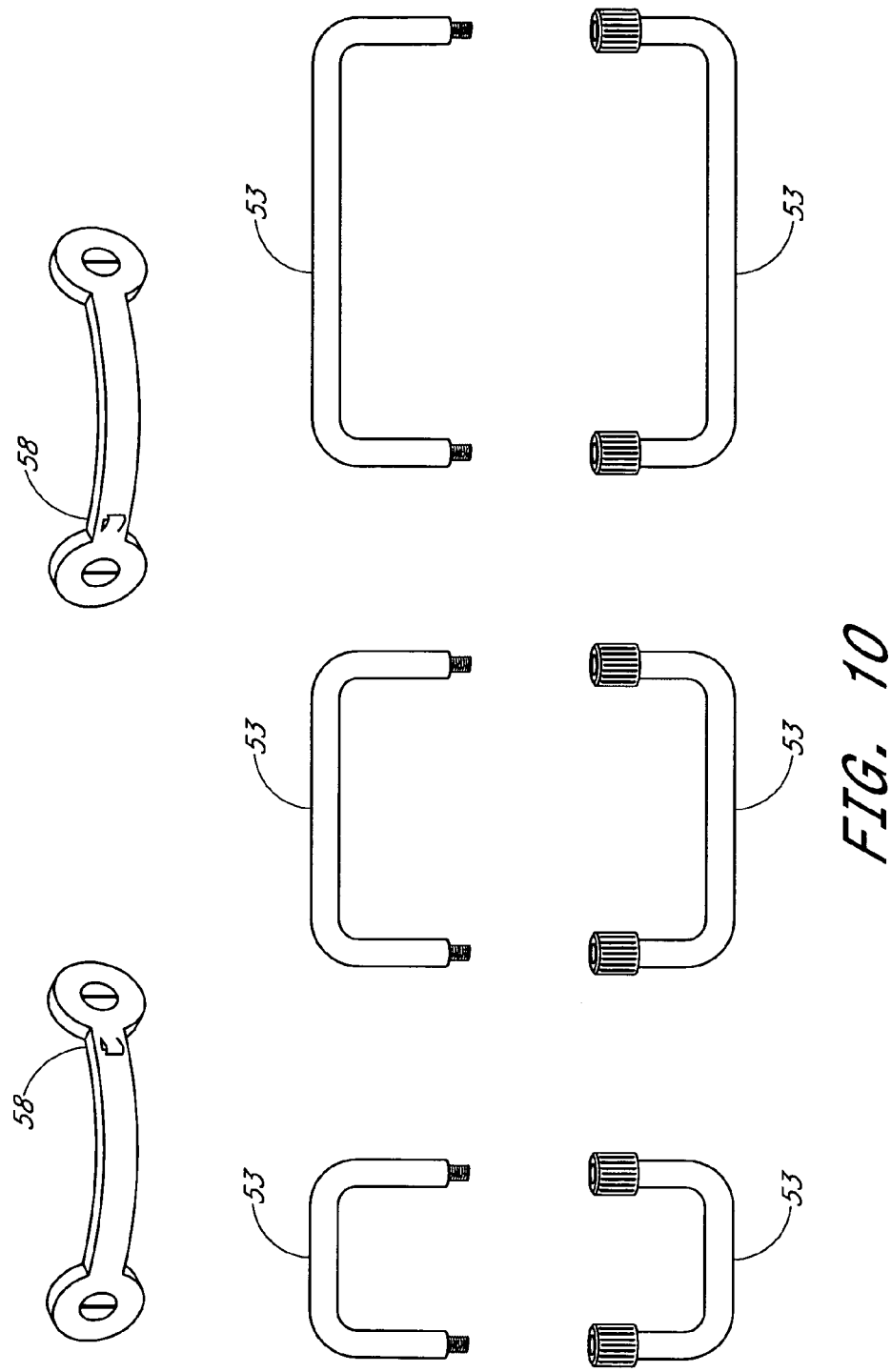
FIG. 10 illustrates another embodiment of the invention with selectable bridge sizes.

In another embodiment depicted in FIG. 8A, the hyoid brace comprises two brace arms 52 and a bridge 53 that is fastenable to the two brace arms 50. The brace arms 52 are attachable to the hyoid bone 15, as shown in FIG. 8B. When fastened to the brace arms 52, the bridge 53 is capable of altering the relative spatial orientation of the brace arms 52. In one embodiment, push members 54 protrude from the inner surface 55 of the bridge 53 to apply force to the medial ends 41 of the brace arms 52. In one embodiment, the bridge 53 has a wider shape than the curvature of the hyoid bone 15 and may spread apart the greater horns 23 of the hyoid bone upon attachment to the brace arms 52. In one embodiment in FIG. 8C, the bridge 53 has both push members 54 and a wider shape. The bridge 53 optionally allows lateral displacement of the hyoid bone in addition to widening of the angle. In still another embodiment, the hyoid bone segments are laterally displaced but the relative angle of the two pieces is generally unchanged. In one embodiment, shown in FIG. 9, lateral displacement is provided by a slotted tongue 54 inserted into a screw mechanism 55. Similarly, anterior-posterior displacement may occur if the tongue 54 and screw mechanism 55 were positioned more laterally along the hyoid bone 15. The bridge 53 attaches to the brace arms 39 by clips 56. In another embodiment in FIG. 10, the operator will select a bridge 53 from a variety of sizes to fasten to the brace arms 52 and alter the separation of the brace arms 52 and the attached hyoid bone. The bridge may attach to the brace arms through eyelets 57 or slots on the outer surface 43 of the brace arms 52. In still another embodiment, the bridge 53 and the brace arms 52 have connectors (not shown) to allow suturing of the hyoid brace to surrounding structures and to further modify the hyoid bone position.

Figure 11A:
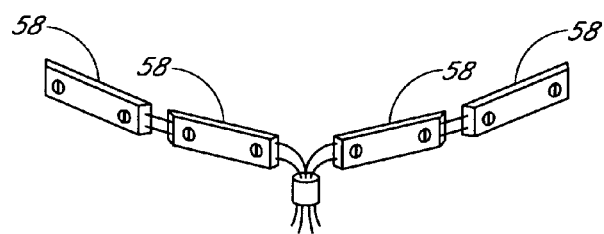
FIG. 11A represents another embodiment of the invention with four brace arms.
Figure 11B:
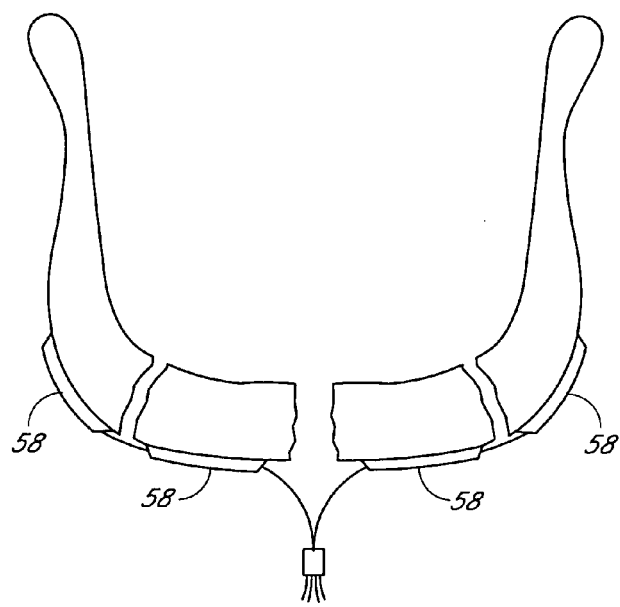
FIG. 11B shows the attachment of the four brace arms to multiple hyoid bone segments and FIG. 11C shows the widening of the hyoid bone segments.
Figure 11C:
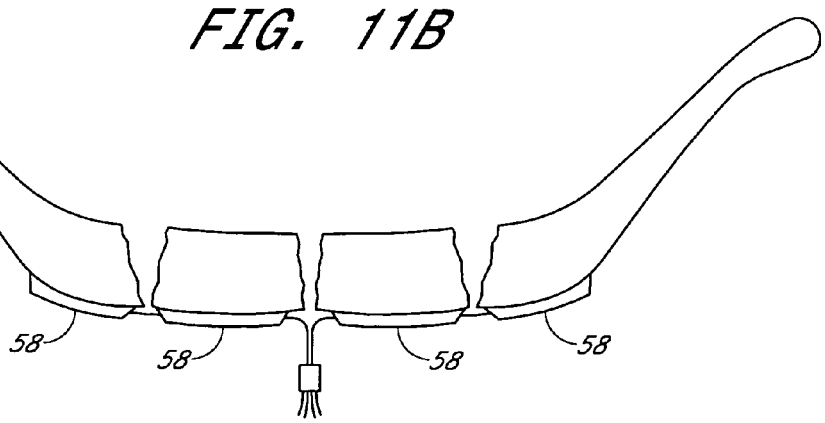

In one embodiment, the hyoid brace may have more than two segments 58 which are attached by two or more pivot joints or bridges, as in FIG. 11.

1. Attachment of the Hyoid Brace to the Hyoid Bone or Bone Segments

In one embodiment, the hyoid brace is attached to the hyoid bone 15 or hyoid bone segments. In one embodiment illustrated in FIG. 12A, bone screws 59 are used to attach the hyoid brace. In another embodiment in FIG. 12B, the attachment occurs with clips 60 on the brace. In another embodiment in FIG. 12D, the brace is attached using sutures or surgical wire 61. In one embodiment in FIGS. 6A and 6B, hooks 62 are used to attach the hyoid brace to the hyoid bone 15. In another embodiment, adhesives are used to attach the hyoid brace. In another embodiment, illustrated in FIG. 6A, a combination of attachments are used.

Figure 12A:
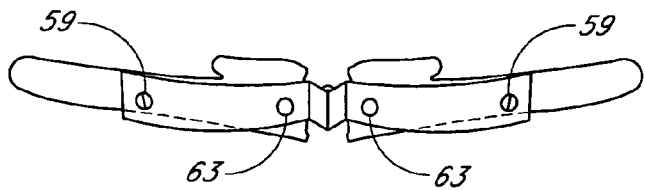
FIGS. 12A through 12D represent various embodiments of attaching the hyoid brace to the hyoid bone.

In one embodiment shown in FIG. 12A, the hyoid brace is attachable to the hyoid bone 15 or bone segments by bone screws 59. The hyoid brace may have one or more screw holes 63 that run from the outer surface to the inner surface 42 of the brace arm 39. In one embodiment, the screw holes 63 or other landmarks on the hyoid brace allow the operator to identify the location of the holes 63 by palpation or by radiographic methods. With the identification of the location of the screw holes, an operator may create additional access for drilling into the hyoid bone 15 or bone segments and for securing the hyoid brace to the hyoid bone 15 or bone segment by inserting a bone screw 59 through the hyoid brace and screw hole 63.

Figure 12B:
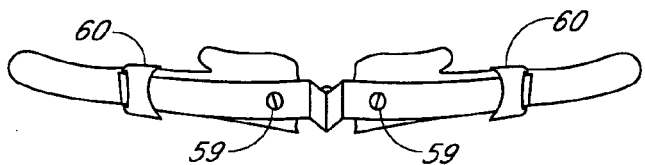
Figure 12C:
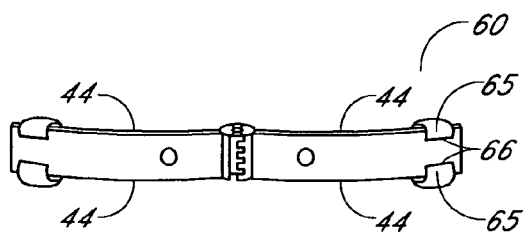
Figure 12D:
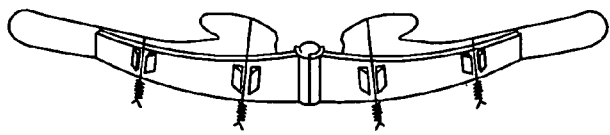

In one embodiment shown in FIGS. 12B and 12C, the hyoid brace comprises clips 60, the clips 60 having a plurality of partially flexible members 64 extending from superior 44 and/or inferior 45 surfaces of the brace arms 39. The partially flexible members 64 have a distal end 65 and a configuration with an inner surface 66 facing the hyoid bone. The configuration may be any path capable of transiting from one point on or about the hyoid bone 15 to another point on or about the hyoid bone that is sufficient to resist displacement of the hyoid brace arms 39 from the hyoid bone 15. The configuration may be a square bracket or a curved clip. The members 64 are sufficiently flexible such that with an application of force against the member 64, the distal ends 65 of the members will flex apart from each other. In one embodiment, where the force results from pressing the brace arm 39 against the hyoid bone 15, the flexion allows the hyoid bone 15 or bone segment to come in proximity of the inner surface of the hyoid brace arm 39. After contact, the flexible members 64 reverts back to their previous configuration and secures the brace arms 39 to the hyoid bone 15 or bone segments.

In one embodiment, sutures 61 are removably attached to the hyoid brace. In one embodiment, depicted in FIG. 12D, the sutures 61 are used to attach the hyoid brace to the hyoid bone 15 or hyoid bone segments. The suture 61 may be cut after the brace arms are attached. Optionally, these sutures 61 may be attached to surrounding structures in the neck or mandible to provide additional support or anchoring of the hyoid brace and hyoid bone. In another embodiment, the sutures may be brought out through the skin to provide additional control of the lateral ends 40 of the brace during the attachment procedure. In one embodiment, the sutures 61 are attached to the lateral ends 40 of the brace arms 39. In another embodiment, sutures 61 are attached to the lateral 40 and medial ends 41 of the brace arms 39.

Figure 6B:
Figure 6C:
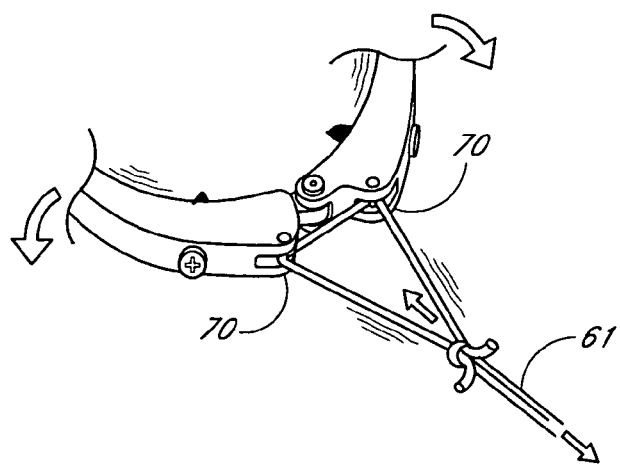

In another embodiment shown in FIGS. 6A and 6B, the hyoid brace comprises at least one hook 62 extending from at least one arm of the hyoid brace. The hook may pierce a portion of the surrounding musculature or connective tissue to engage the hyoid brace with the hyoid bone 15 to at least partially hold the hyoid brace next to the hyoid bone 15. In one embodiment, the hyoid brace is positioned adjacent to the hyoid bone 15 and then rotated about its longitudinal access until the hooks engage around the hyoid bone. A portion or all of the brace arm 52 may comprise a helical configuration, so that it may be distally advanced with rotation to encircle the corresponding greater horn 23 of the hyoid bone 15.

In another embodiment, an interference fit is provided between the hyoid brace and hyoid bone by creating a passage through at least a portion of the hyoid bone and inserting the brace arm or extension therefrom into the passage. In one embodiment, the passage is created through an inner core of the hyoid bone. In another embodiment, the passage extends between an outer anterior or lateral surface of the hyoid bone and an inner surface of the hyoid bone. A hyoid brace inserted into the passage from the outer to inner surface of the hyoid bone allows manipulation of the hyoid brace to apply a, outward force to the inner surface of the hyoid bone. Alternatively, the hyoid brace may originate from about the outer anterior surface of the hyoid bone, extend bilaterally over the superior or inferior surfaces to contact the inner surfaces of the hyoid bone and apply a radially outward force.

In another embodiment of the present invention, the hyoid brace is adapted for implantation in the tissue adjacent to the hyoid bone or other tissue comprising the pharynx. The pharynx, as used herein, is given its ordinary meaning and also includes the pharyngeal mucosa, pharyngeal submucosa, pharyngeal musculature, hyoid bone, infrahyoid muscles, suprahyoid muscles and any connective tissue between. The brace is inserted into the soft tissue adjacent to the hyoid bone or pharyngeal wall and manipulated to exert sufficient force to dilate portions of the pharyngeal wall or support the pharyngeal walls from collapse. The screws, clips, hooks or sutures of the previous embodiments of the invention or other soft tissue anchors may be adapted to secure the brace to the soft tissue of the pharyngeal wall. In another embodiment, the implant resides within and relies on the natural fascial planes of the neck musculature to affix its position and does not require any additional attachment to muscle. In one embodiment, the brace arms are inserted into fascial planes between the stylohyoid and hyoglossus muscles. In another embodiment, the brace arms are inserted into the fascial planes between the hyoglossus and mylohyoid muscles. In another embodiment, the brace arms are inserted posterior to the posterior belly of the digastric muscle and anterior to the stylohyoid muscle. In still another embodiment, the brace arms are placed between the superior belly of the omohyoid and thyrohyoid muscles. The brace arms are then manipulated to achieve a lateral separation and then locked or caused by internal bias to retain their relative positions.

2. Configuration Lock of the Hyoid Brace

In one embodiment, shown in FIGS. 13A and 13B, a configuration lock 67 is located between the two brace arms 39 and is attachable to both brace arms 39. The configuration lock 67 comprises a locking member 68 with at least one interfaceable end 69 and at least one locking interface 70 located on a brace arm 39. When the interfaceable end 67 of the locking member 68 is in contact with the locking interface 70 of the brace arms 39, the locking member 68 limits the movement, if any, of a brace arm 39 relative to the other brace arm 39 or brace arms 39.

In one embodiment, the locking member 68 comprises an elongated member 71 with two interfaceable ends 67 at least one of which comprises a threaded end 72. Each brace arm 39 has an interface for receiving the member 71, at least one of which has a locking interface 70 comprising a threaded hole 73. The threaded hole 73 is matched to the threaded ends 72 of the elongated member 71 such that the elongated member 71 may pass axially through the threaded hole 73 by applying a rotation force to the elongated member 71. In one embodiment, the locking interface 70 comprises a threaded hole 73 within a cavity 74 of the brace arm 39. The cavity 74 may have one or more openings 75. When the threaded ends 72 of the elongated member 71 are screwed into the threaded locking interfaces 70, the relative position and angle formed by the brace arms 39 may be fixed. In one embodiment, the position and angle may be reversibly adjusted by rotating the elongated member 71. In one embodiment, the locking interface 70 comprises a threaded hole 73 in a protrusion 76 from the brace arm 39, shown in FIGS. 14A and 14B.

As is illustrated herein, a variety of different configurations of the implant may be devised in which a rotatable threaded shaft 71, depicted in FIG. 15A, is utilized both to adjust the angular orientation of the implant, as well as retain the implant in a predetermined orientation. This allows the clinician to rotate a driver tool 78, represented in FIG. 15C, coupled to the rotatable shaft 71 thereby adjusting the angular orientation of the implant throughout a continuous range. Once the desired manipulation of the hyoid bone 15 has been accomplished, the deployment tool 78 may be decoupled from the rotatable shaft 71, and the implant will retain its predetermined configuration.

The adjustment tool 78 (e.g., an elongate rotatable shaft having an anti-rotation coupling thereon for interlocking with a corresponding complementary interlocking surface on the rotatable shaft 71) may be oriented coaxially with the rotatable shaft 71. In this configuration, a linear coaxial access lumen is preferably provided such as by lengthening the lumen or threaded hole 73 along its longitudinal axis through the implant until it exits the implant, thereby enabling direct axial connection of the adjustment tool. This lateral approach is illustrated, for example, in FIG. 15E, however may be applied to any of the rotational embodiments herein.

Alternatively, it may be desirable to adjust the implant from an anterior approach. In this configuration, a 90° or other bend in the axis of rotation may be provided, utilizing gear mechanisms well understood in the art, allowing the rotation of an adjustment tool which lies along an anterior-posterior axis to translate rotation into the elongated member 71, which lies in a lateral axis perpendicular or at a non normal angle to the anterior-posterior axis.

Figure 15D:
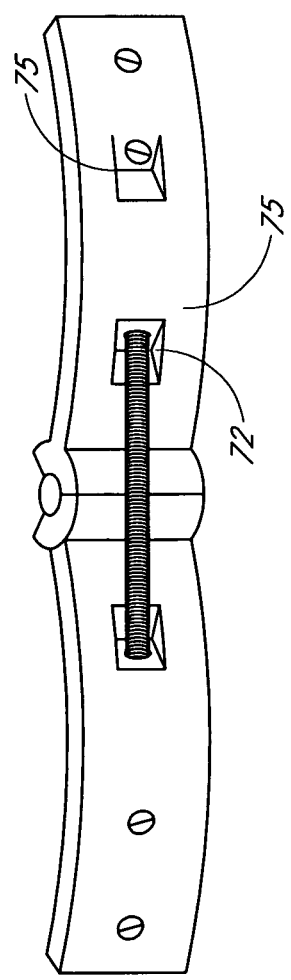
FIGS. 15D and 15E are anterior and superior views of one embodiment of the invention utilizing the locking member with the rotational interface.
Figure 15E:
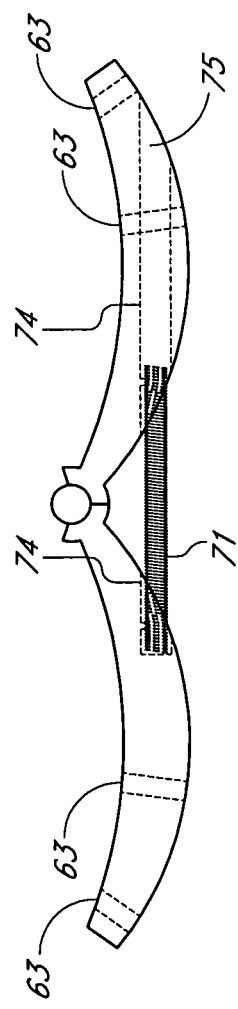

In one embodiment, represented in FIG. 15A, one or both of the threaded ends 72 may optionally have a rotation interface 77, as in FIG. 15B, so that the tool 78, seen in FIG. 15C with a complementary interface 79 can be applied to the threaded end 72 to facilitate rotation of the elongated member 71. The rotation interface 77 may comprise a slot in the end of the elongated member 71 and the tool 78 comprises a screwdriver with a complementary interface 79 comprising a flat end fittable to the slot. In another embodiment, the rotation interface 77 is a hex or other noncircular configuration recess or projection head and the tool 78 is a hex screwdriver or other complementary surface structure. In one embodiment, depicted in FIGS. 15D and 15E, the cavity 74 containing the locking interface 70 has at least two openings 75. One opening 75 accepts the threaded end 72 of the elongated member 71. Another opening 75 provides access to the rotation interface 77 of the elongated member 71.

As will be appreciated in view of the disclosure herein, rotation of the elongated member 71 in a first rotational direction will advance the elongated member 71 distally along its longitudinal axis, thereby closing the angle between the first and second arms of the implant. Rotation of the elongated member 71 in an opposite direction will enable opening of the angle between the first and second arms of the implant. In this manner, the angular orientation of the arms of the implant may be adjusted throughout an angular range.

In another embodiment, the elongated member 71 further comprises a grippable surface between the two threaded ends 72. In one embodiment, illustrated in FIG. 16A, the grippable surface comprises a dial 81. In one embodiment, shown in FIG. 16B, the grippable surface comprises two or more flat surfaces 82 along the elongated member 71.

Figure 17A:
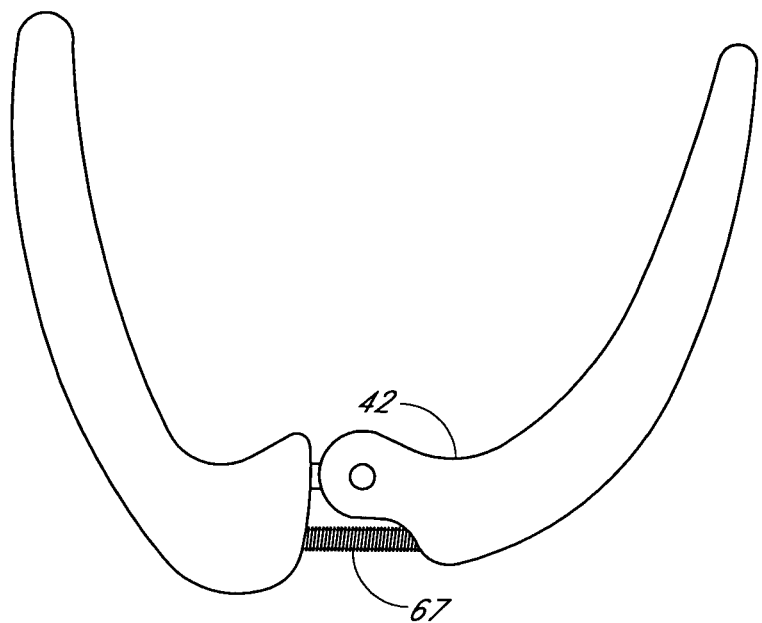
FIGS. 17A and 17B represent embodiments of the invention shows the relative position of the pivot joint and the configuration lock.
Figure 17B:
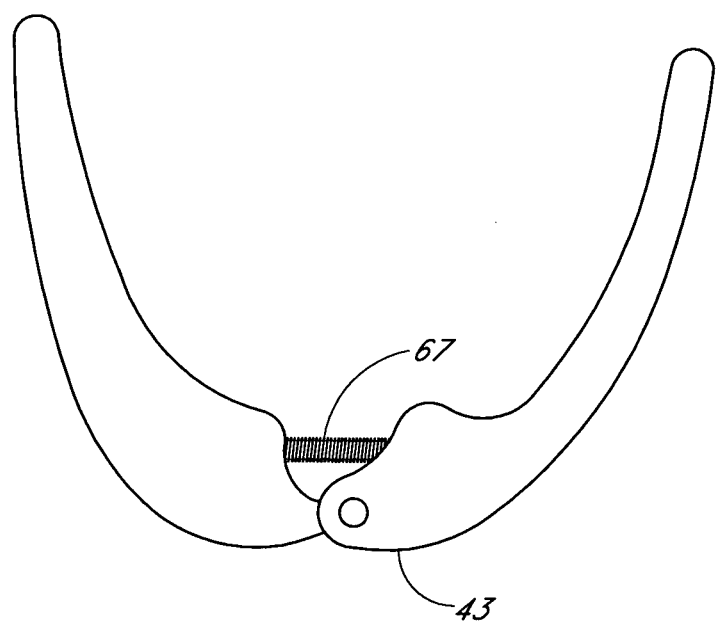

In one embodiment, depicted in FIG. 17A, the pivot joint of the hyoid brace is located closer to the inner (posterior) surface 42 of the hyoid brace relative to a configuration lock 67. In another embodiment, represented in FIG. 17B, the pivot joint is located closer to the outer (anterior) surface 43 of the hyoid brace relative to the configuration lock 67. Thus, the threaded shaft 67 may be located such that it is either under tension or under compression while restraining the hyoid bone in its modified orientation.

Figure 18A:
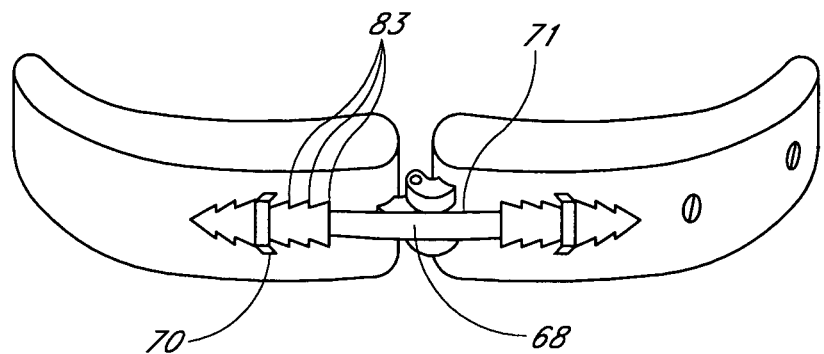
FIGS. 18A and 18B illustrate other embodiments of the configuration lock using semi-flexible locking members.
Figure 18B:
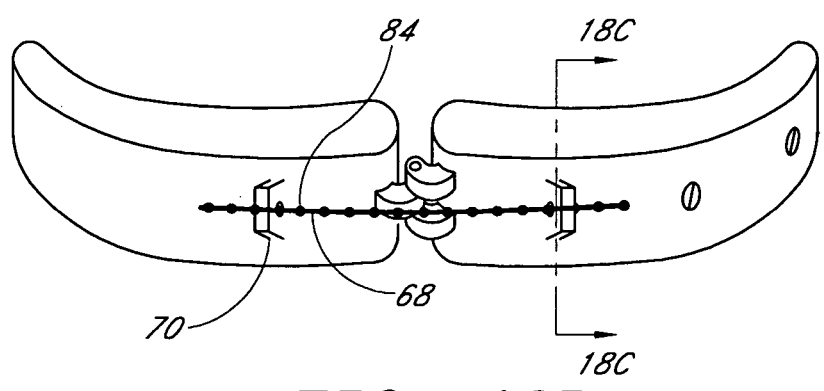
Figure 18C:
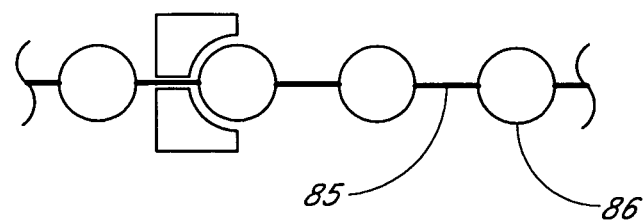
FIG. 18C is a cross sectional view of the locking interface for the locking member of FIG. 18B.

In another embodiment, shown in FIG. 18A, the locking member 68 comprises an elongated member 71 that is semi-flexible and has a ramped surface 83 that allows insertion through a locking interface 70 in one direction but acts as a ratchet to resist movement in the opposite direction. In another embodiment, illustrated in FIG. 18B, the locking member 68 comprises a beaded wire 84 with a locking interfaces 70 that allows passage of wire 85 but not beads 86, as seen in FIG. 18C.

In one embodiment, one or more locking interfaces 68 may provide some relative movement between itself and the brace arm 39 to which it is attached. This relative movement may be desirable to accommodate angular changes in the position between the locking member 68 with the brace arm 39 as the configuration lock 67 is adjusted to the desired position. In one embodiment, illustrated in FIG. 19A, the locking interface 70 provides some relative movement through limited flexibility of a protrusion 76 of the brace arm 39. In another embodiment, relative movement is provided by hinge joints (not shown) attaching the locking interfaces to the brace arms. In another embodiment, depicted in FIG. 19B, some relative movement is provided by a threaded nut 87 in a cavity 74 of the brace arm 39 that is slightly loose in the cavity 74 to allow some tilting of the threaded nut 87, but is not enough to allow rotation or longitudinal displacement of the nut 87 within the cavity 74. The cavity 74 may provide entry of the locking member 68 at a range of angles.

Figure 20A:
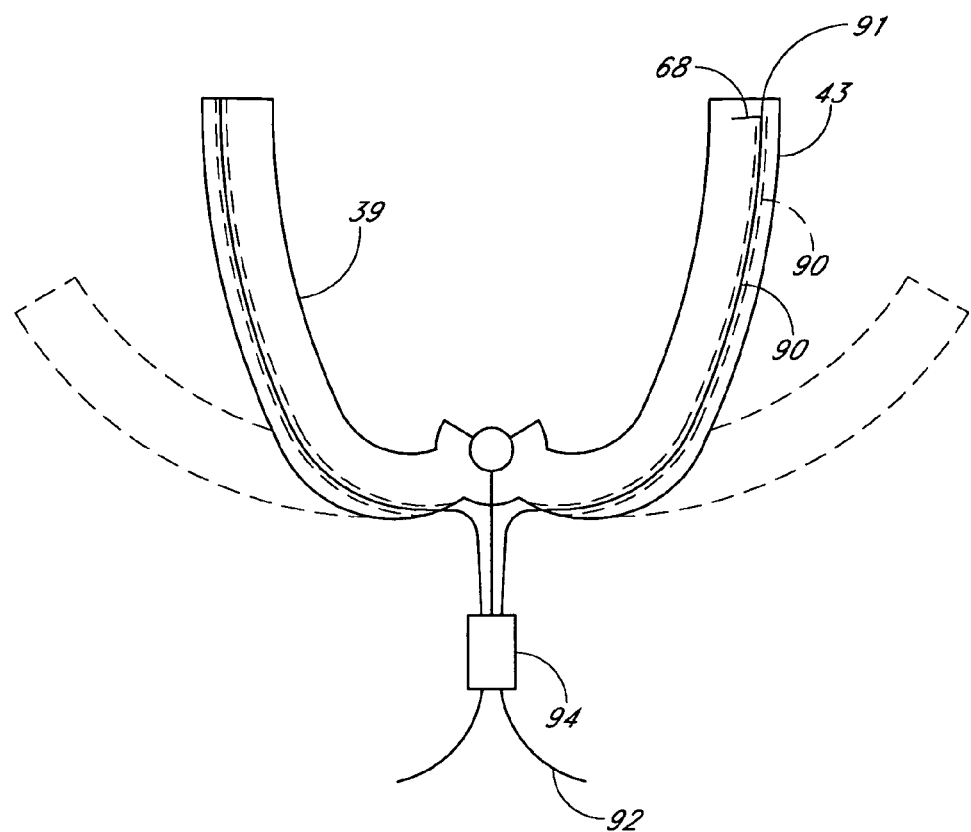
FIGS. 20A and 20B show embodiments of the invention with partially flexible brace arms and a wire-based configuration lock.
Figure 20B:
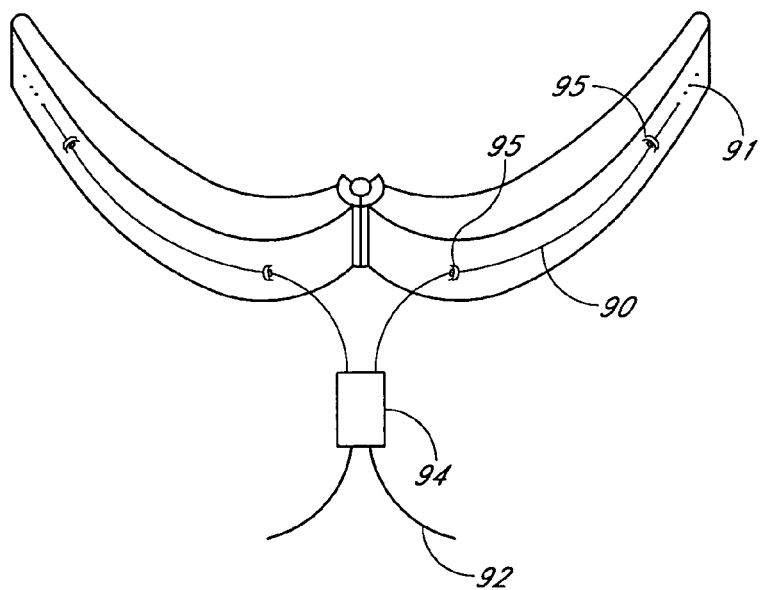

In another embodiment, depicted in FIG. 20A, the brace arms 39 of the hyoid brace are pivotable and/or semi-flexible and the locking member 68 comprises wires 90 with proximal 91 and distal ends 92 that are slideable along conduits 93 located in the brace arms 39 closer to the outer surface 43, and a cinching member 94 that controls the sliding of wires 90. The locking interfaces 68 of the brace arms 39 comprise an attachment of the distal ends 92 of the wires 90 to the lateral ends 40 of the brace arms 39. As the wires 90 are pulled from a lateral to medial direction, the inner 42 and outer surfaces 43 of the brace arms 39 will shift at different rates and cause the brace arms 39 to flex outward and widen the angle formed by the attached hyoid bone 15 or hyoid bone segments. In another embodiment, shown in FIG. 20B, the conduits 93 comprise a plurality of eyelets 95 protruding from the outer surface 43 of the brace arms 39. In another embodiment shown in FIGS. 11A to 11C, more than two brace arms 39 are used with the wire-based configuration lock. In one embodiment, the cinching member 94 may reversibly control the sliding of the wires 90 through reversible friction. In another embodiment, the cinching member 94 reduces sliding of the wires 90 through heating bonding to the wires 90.

In another embodiment, represented in FIGS. 21A and 21B, the locking interface comprises a plurality of holes 96 on the brace arms 39 with the configuration lock comprising at least one suture 97 threaded between holes 96 on two different brace arms 39.

In one embodiment, as shown in FIG. 22A, a torsion spring 98 is located about a hinge joint 47. The torsion spring 98 has two ends 99, depicted in isolation in FIG. 22B, that extend distally to apply force to the brace arms 39 to widen the angle formed by the brace arms to the maximum allowed by the hinge joint. The ends 99 of the torsion spring 98 may be embedded within the brace arms 39 or the ends 99 may found external to the brace arms 39 against the inner surface 42 of the brace arms. The spring tension may be selected to allow at least narrowing of the angle formed by the brace arms during swallowing or speaking.

3. Materials for Construction of the Hyoid Brace

For the embodiments discussed herein, the hyoid brace, together with the configuration lock and other components of the present invention can be manufactured in accordance with any of a variety of techniques which are well known in the art, using any of a variety of medical-grade construction materials. For example, the hyoid brace and other components of the present invention can be injection-molded from a variety of medical-grade polymers including high or other density polyethylene, nylon and polypropylene. Portions of the configuration lock can be separately formed from the brace arms and secured thereto in a post-molding operation, using any of a variety of securing techniques such as solvent bonding, thermal bonding, adhesives, interference fits, pivotable pin and aperture relationships, and others known in the art. Preferably, however, the configuration lock is integrally molded with the brace arms, if the desired material has appropriate physical properties.

A variety of polymers which may be useful for the hyoid brace components of the present invention are identified below. Many of these polymers have been reported to be biodegradable into water-soluble, non-toxic materials which can be eliminated by the body:

Polycaprolactone
Poly (L-lactide)
Poly (DL-lactide)
Polyglycolide
Poly (L-Lactide-co-D, L-Lactide)
70:30 Poly (L-Lactide-co-D, L-Lactide)
95:5 Poly (DL-lactide-co-glycolide)
90:10 Poly (DL-lactide-co-glycolide)
85:15 Poly (DL-lactide-co-glycolide)
75:25 Poly (DL-lactide-co-glycolide)
50:50 Poly (DL-lactide-co-glycolide)
90:10 Poly (DL-lactide-co-caprolactone)
75:25 Poly (DL-lactide-co-caprolactone)
50:50 Poly (DL-lactide-co-caprolactone)
Polydioxanone
Polyesteramides
Copolyoxalates
Polycarbonates
Poly (glutamic-co-leucine)

The desirability of any one or a blend of these or other polymers can be determined through routine experimentation by one of skill in the art, taking into account the mechanical requirements, preferred manufacturing techniques, and desired reabsorption time. Optimization can be accomplished through routine experimentation in view of the disclosure herein.

Alternatively, the hyoid brace components can be molded, formed or machined from biocompatible metals such as Nitinol, stainless steel, titanium, and others known in the art. In one embodiment, the components of the hyoid brace are injection-molded from a bioabsorbable material, to eliminate the need for a later removal step or to promote fibrosis and fixation of adjacent structures. One suitable bioabsorbable material which appears to exhibit sufficient structural integrity for the purpose of the present invention is poly-p-dioxanone, such as that available from the Ethicon Division of Johnson & Johnson. Poly (L-lactide, or co-DL-lactide) or blends of the two may alternatively be used. As used herein, terms such as bioabsorbable, bioresorbable and biodegradable interchangeably refer to materials which will dissipate in situ, following a sufficient post-operative period of time, leaving acceptable byproducts. Bodily reaction to the bioabsorbable materials or byproducts may furnish at least a portion of the support provided by the device or treatment method. All or portions of any of the devices herein, as may be appropriate for the particular design, may be made from allograft material, or synthetic bone material.

The bioabsorbable implants of this invention can be manufactured in accordance with any of a variety of techniques known in the art, depending upon the particular polymers used, as well as acceptable manufacturing cost and dimensional tolerances as will be appreciated by those of skill in the art in view of the disclosure herein. For example, any of a variety of bioabsorbable polymers, copolymers or polymer mixtures can be molded in a single compression molding cycle, or the surface structures can be machined on the surface of the hyoid brace after the molding cycle. It is also possible to use the techniques of U.S. Pat. No. 4,743,257, the entire disclosure of which is incorporated herein by reference, to mold absorbable fibers and binding polymers together.

An oriented or self-reinforced hyoid brace can also be created during extrusion or injection molding of absorbable polymeric melts through a suitable die or into a suitable mold at high speed and pressure. When cooling occurs, the flow orientation of the melt remains in the solid material as an oriented or self-reinforcing structure. The mold can have the form of the finished brace component, but it is also possible to manufacture the brace components of the invention by machining injection-molded or extruded semifinished products. It may be advantageous to make the hyoid brace from melt-molded, solid state drawn or compressed, bioabsorbable polymeric materials, which are described, e.g., in U.S. Pat.

Nos. 4,968,317 and 4,898,186, the entire disclosures of which are incorporated herein by way of this reference.

Reinforcing fibers suitable for use in the components of the present invention include ceramic fibers, like bioabsorbable hydroxyapatite or bioactive glass fibers. Such bioabsorbable, ceramic fiber reinforced materials are described, e.g., in published European Patent Application No. 0146398 and in WO/96/21628, the entire disclosures of which are incorporated herein by way of this reference.

As a general feature of the orientation, fiber-reinforcement or self-reinforcement of the brace components, many of the reinforcing elements are oriented in such a way that they can carry effectively the different external loads (such as tensile, bending and shear loads) that are directed to the hyoid brace as used.

The oriented and/or reinforced hyoid brace materials for many applications have tensile strengths in the range of about 100-2000 MPa, bending strengths in the range of about 100-600 MPa and shear strengths in the range of about 80-400 MPa, optimized for any particular design and application. Additionally, they are relatively stiff and tough. These mechanical properties may be superior to those of non-reinforced or non-oriented absorbable polymers, which often show strengths between about 40 and 100 MPa and are additionally may be flexible or brittle. See, e.g., S. Vainionpaa, P. Rokkanen and P. Tormnld, "Surgical Applications of Biodegradable Polymers in Human Tissues", Progr. Polym. Sci., Vol. 14, (1989) at 679-716, the full disclosure of which is incorporated herein by way of this reference. In other embodiments of the present invention, a semi-flexible material is desired to provide a resilience so that normal swallowing and speaking are not impaired.

The brace components of the invention (or a bioabsorbable polymeric coating layer on part or all of the brace surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

C. Placement of a Hyoid Brace

1. Surgical Approach

Figure 23A:
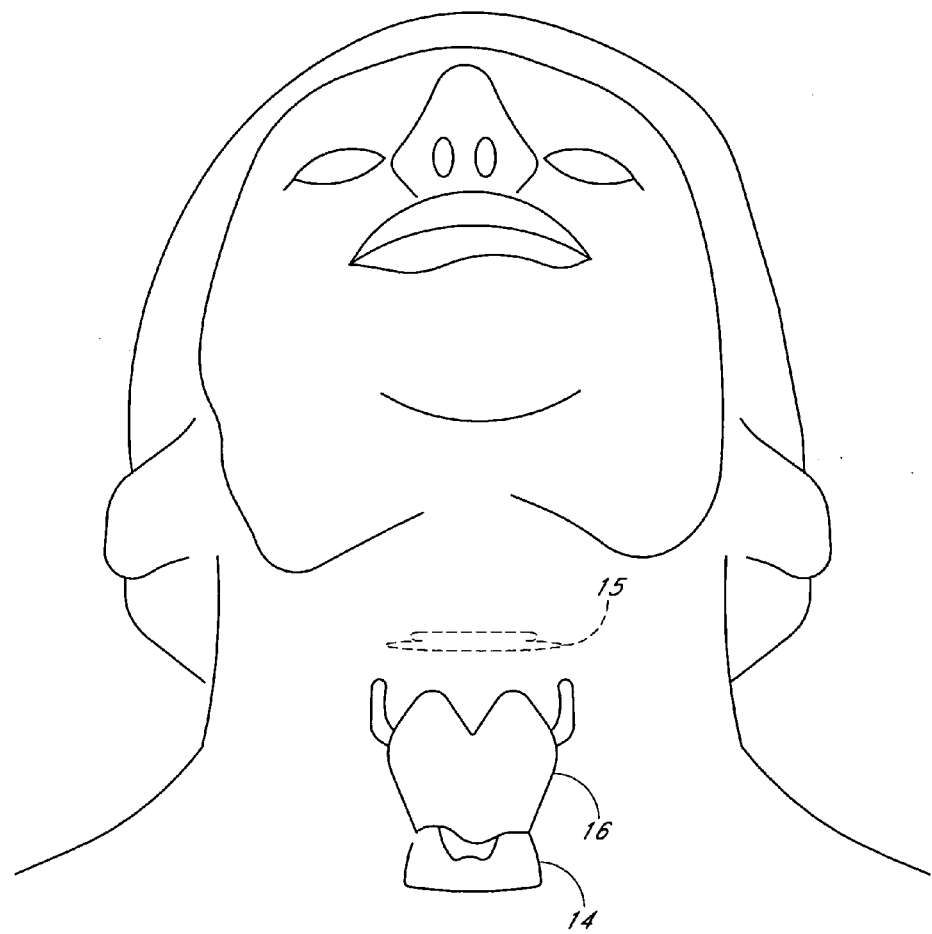
FIG. 23A shows the anatomical position of the hyoid bone relative to the thyroid cartilage and other landmarks of the head and neck.
Figure 23B:
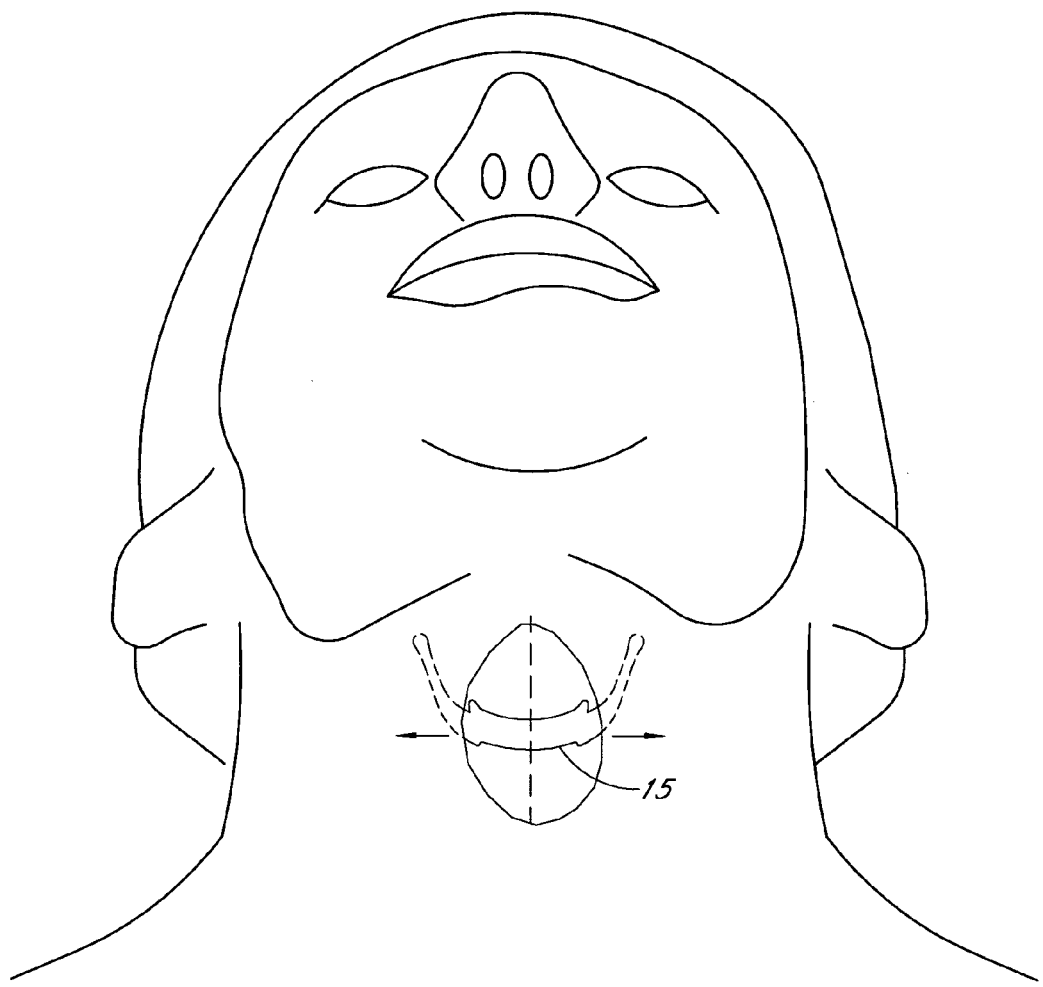
FIGS. 23B through 23G represents at least one embodiment of the invention comprising an attachment of separate brace arms to the hyoid bone, joining the two brace arms and generally fixing their relative spatial position with suture or surgical wire.
Figure 23C:
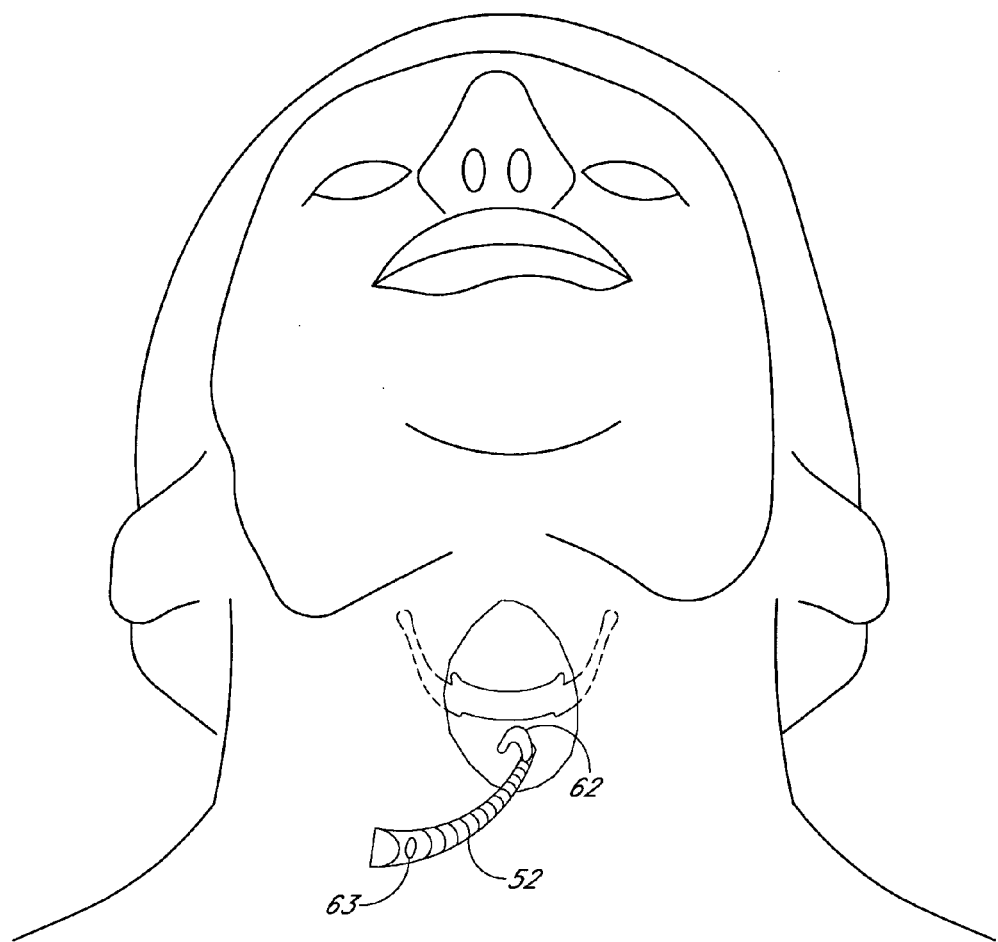
Figure 23D:
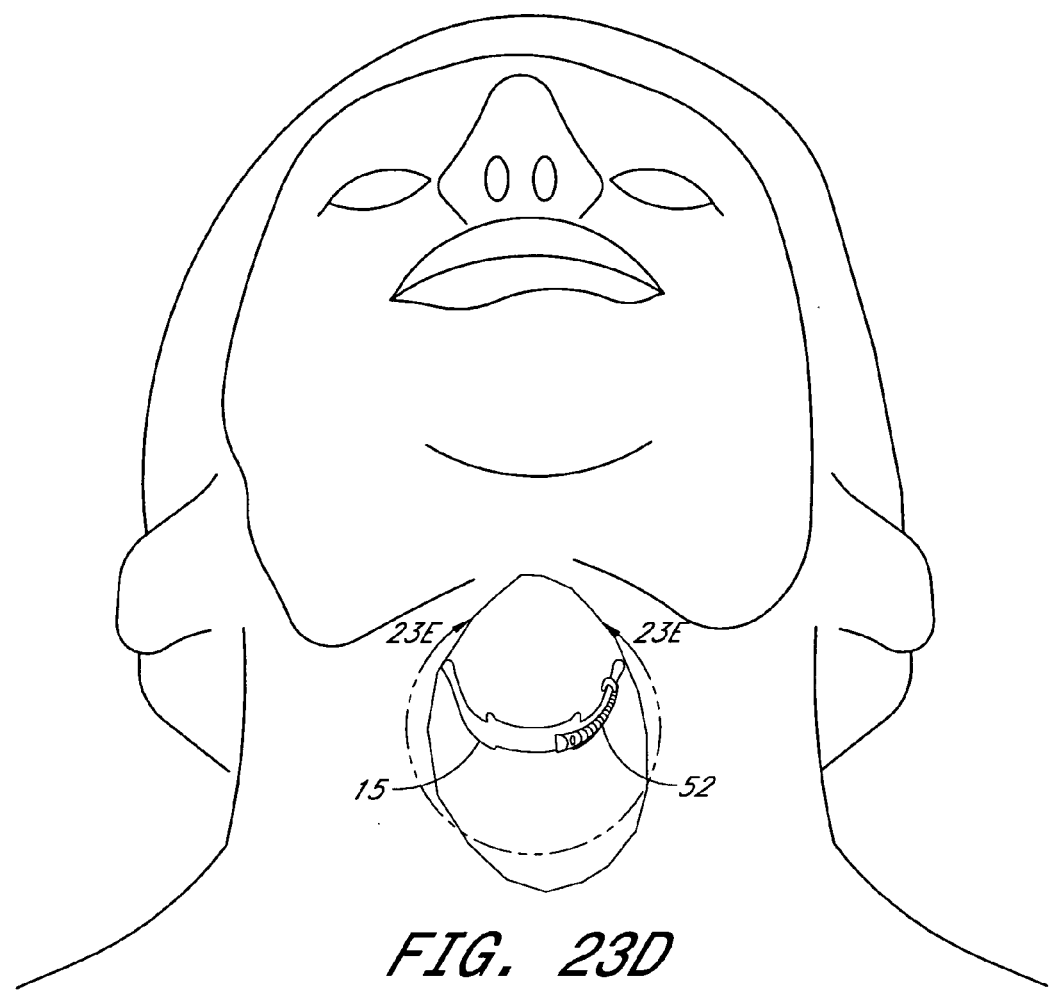
Figure 23E:
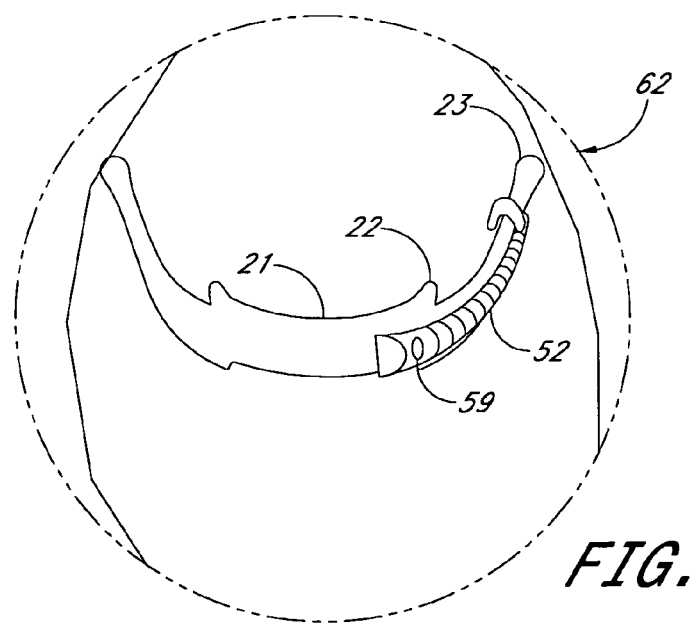
Figure 23F:
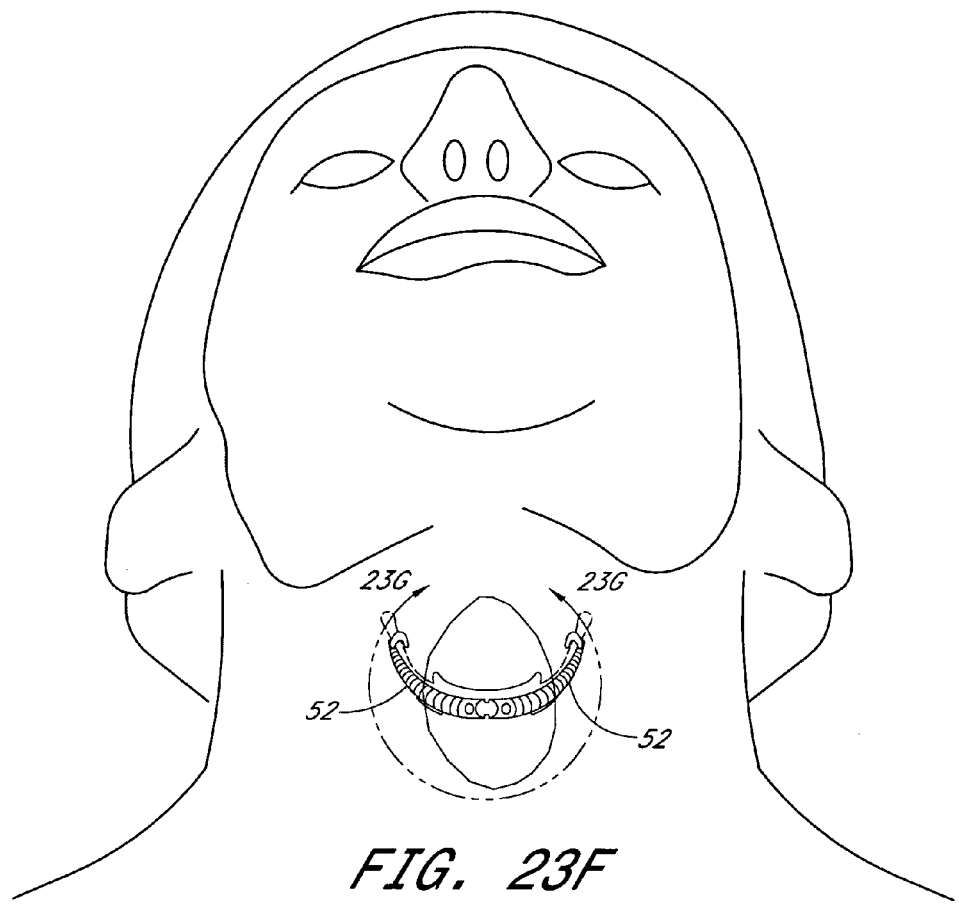
Figure 23G:
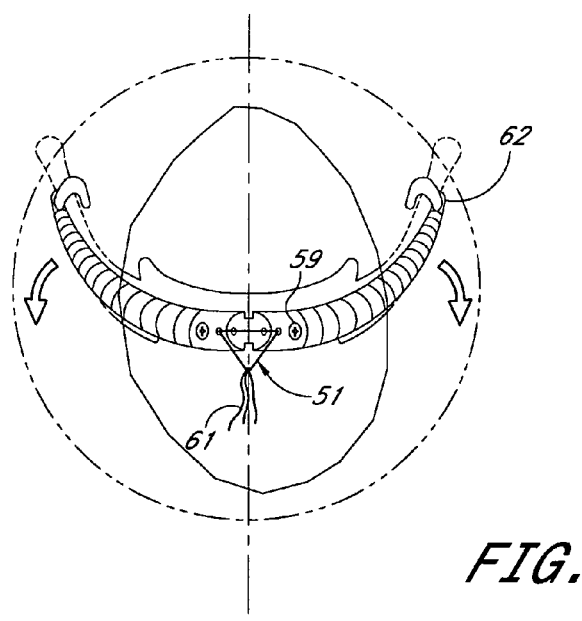

In one embodiment as depicted in FIG. 23A, the head of the patient is placed in an extended position to facilitate access to the upper neck. The skin of the neck is sterilized and draped using procedures well known to those with skill in the art. Applying sterile technique and using the thyroid cartilage 16 as a landmark, the hyoid bone 15 is palpated, if possible, and an incision site is identified about the midline of the hyoid bone. In one embodiment, the skin is injected with anesthetic containing epinephrine until anesthesia is achieved. About a 2 to about a 5 cm incision is made in the skin generally overlying the midportion of the hyoid bone 15. In one embodiment, the incision is a vertical incision, shown in FIG. 23B. In another embodiment, the incision is a horizontal incision. The subcutaneous tissue is dissected until the platysma muscle is reached. Skin retractors are used to maximize and maintain the visibility of the exposed incision site. At least a 1 cm vertical midline incision is made in the platysma muscle to expose at least a portion of the hyoid bone. Blunt dissection is then performed along the hyoid bone 15 to each lateral side of the incision site to create a dissected space and to facilitate insertion of a hyoid brace along the anterior surface of the hyoid bone 15. Muscles attached to the hyoid bone may be transected to facilitate visibility of the surgical site, attachment of the hyoid brace, expansion of the pharyngeal airway, or to alter the movement of the hyoid bone, but is not limited to any these particular purposes. The hyoid brace is then attached to the hyoid bone as previously described and illustrated in FIGS. 23C through 23G. In one embodiment, additional access sites are created to the dissected space. Additional access sites may be created by passing an instrument from the dissected space out through the skin of the neck. In another embodiment, access sites are created by puncturing the skin of the neck and inserting an instrument to the dissected space. Other variant approaches will be apparent to those skilled in the art, such as otolaryngologists, including endopharyngeal approaches. In another embodiment, a midline incision is made in the skin about 2 to about 4 cm above the hyoid bone and the subcutaneous tissue is dissected until the suprahyoid muscles are reached. The brace is attached to the suprahyoid musculature or inserted into fascial planes between the suprahyoid muscles. The suprahyoid muscles may be dissected further to implant the brace closer to the inner wall of the pharynx. In another embodiment, the midline incision is made about 1 to about 4 cm below the hyoid bone and the brace is inserted into or attached to the infrahyoid musculature.

Figure 24A:
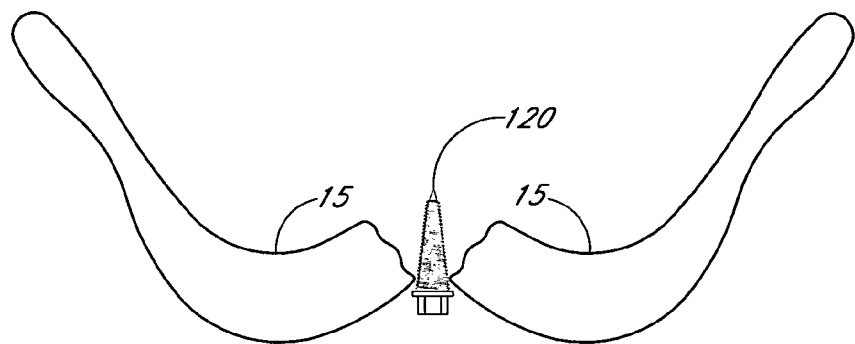
FIGS. 24A through 24C depict various embodiments of spacers that may be used with the invention.
Figure 24B:
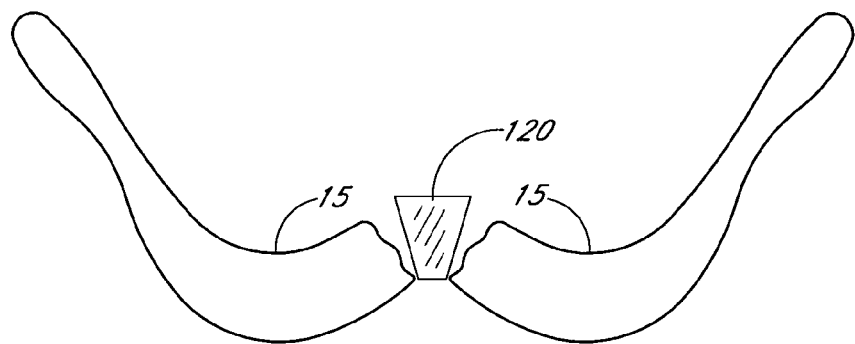
Figure 24C:
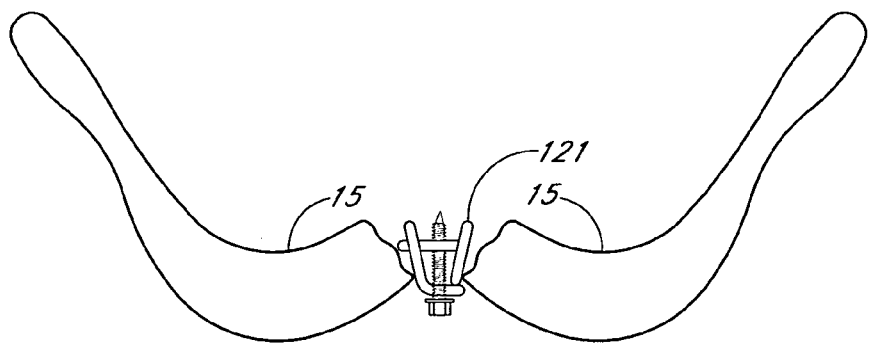
Figure 24D:
FIG. 24D is an oblique view of an adjustable spacer in FIG. 23C.

In one embodiment, the hyoid bone 15 is not cut but is bent to a wider angle. In another embodiment, the hyoid bone 15 is cut prior to the insertion of the hyoid brace. In another embodiment the hyoid bone 15 is cut after the insertion of the hyoid brace into the dissection space but prior to the attachment of the hyoid brace to the hyoid bone 15. In still another embodiment, the hyoid bone 15 is cut after the brace is attached to the hyoid bone 15. In another embodiment, the brace is adjustable after attachment to the hyoid bone 15 such that position and angle of the hyoid bone segments may be reversible changed at any time. In one embodiment, the segments of the hyoid bone 15 may immediately assume the desired position and angle after cutting from of the forces applied to the hyoid bone segments by the attached brace. In one embodiment the hyoid bone 15 is cut at about the midline. In another embodiment the hyoid bone is cut anywhere between the lesser horns. In another embodiment the hyoid bone is cut anywhere between the greater horns. In another embodiment, the hyoid bone is cut into multiple segments. In another embodiment the hyoid bone is cut twice, with each cut made just at or about medial to each lesser horn. In one embodiment, illustrated in FIGS. 24A and 24B, a spacer 120 is inserted between or about the hyoid bone segments. In one embodiment, represented in FIGS. 24C and D, the spacers 121 are adjustable in size after insertion. In another embodiment, graft materials (not shown) are inserted between or about the hyoid bone segments. The graft material may be an autograft, allograft, xenograft or synthetic. Synthetic graft material be ceramic-based, silicon-based or calcium-based. The graft material may also include osteoinductive factors to promote bone ingrowth. In another embodiment, spacers and synthetic graft material are inserted between or about the hyoid bone segments. One skilled in the art will appreciate that there are many varieties of synthetic graft materials and constituents that may be used to between or about the hyoid bone segments.

In one embodiment, the brace is adjustable after attachment to the hyoid bone 15 such that position and angle of the hyoid bone segments may be reversibly changed at any time. In one embodiment, after the hyoid brace is attached to the hyoid bone 15 or bone segments, the attachment of the brace is checked and adjusted if necessary and the incision and puncture sites are closed as known by those skilled in the art. In one embodiment the incision sites are closed by sutures. In another embodiment the incision sites are closed by adhesives. In another embodiment, the wound is covered with dressings. In one embodiment, airway patency is assessed during the procedure and for a period of time after the procedure to ensure stability of the brace and hyoid bone. In one embodiment, sutures are optionally used to permanently or temporarily stabilize the hyoid bone or bone segments for attachment of the hyoid brace. The sutures are placed around the hyoid bone so that the free ends of the sutures extend outside the body and the operator may apply a pulling force to the sutures to resist any inward force applied to the hyoid bone or bone segment during the attachment process. Alternatively, the sutures may be attached to other structures of the body.

In one embodiment, the apparatus and method for hyoidplasty is adapted to repair a fractured hyoid bone resulting from neck trauma.

2. Minimally Invasive Approach a. Delivery Member for the Hyoid Brace

One embodiment of the invention, shown in FIG. 25A, comprises a delivery member 100 having a core 101 with a proximal end 102 and a distal end 103, an outer sheath 104 with a proximal end 105 and a distal end 106 and a fastener with a proximal end 108 and distal end 109. In one embodiment, the delivery member 100 is a flexible catheter. In another embodiment, the delivery member is a rigid instrument. In one embodiment, the delivery member 100 further comprises a handle 110 at the proximal end 102 of the core 101. The delivery member 100 has sufficient rigidity to direct the placement of the hyoid brace or brace components through various thicknesses of subcutaneous tissue. The hyoid brace or brace components are attachable to the distal end 103 of the core 101 by a fastener 107. In one embodiment, the fastener 107 comprises a clamp 111 or forceps attached to the distal end 103 of the core 101 that may be optionally controlled by the proximal end 108 of the fastener 107 located at the proximal end 102 of the core 101 through a push button 112 or a squeeze lever that releases the clamp 111 or forceps, as is known to those skilled in the art. In another embodiment, depicted in FIG. 25B, the fastener 107 is a wire 113 or suture that extends through the core 101 from proximal to distal, loops around the hyoid brace near the medial ends of the hyoid brace and extends back through the core 101 from distal to proximal. Both ends of the wire 113 or suture are located at the proximal end 102 of the core 101 and are attached to a proximal anchor 115. In one embodiment, the wire 113 or suture is sufficiently taut to hold a portion of the hyoid brace against the distal end 103 of the core 101. A outer sheath 104 is positioned around the distal end of the core, having an extended position and a retracted position. In the extended position, the outer sheath 104 generally overlies the hyoid brace. In one embodiment, the outer sheath 104 in the extended position prevents the hyoid brace from changing from an unfolded position to a folded position. In the retracted position, the hyoid brace is generally exposed and the outer sheath 104 does not prevent the hyoid brace from unfolding. In one embodiment, an outer projection 116 on the core 101 and an inner projection 117 on the outer sheath 104 block the outer sheath 104 from extending past an extended position. The hyoid brace is releasable from the distal end 103 of the core 101 by freeing one end of the wire 113 or suture and pulling the wire 113 proximally to remove the loop of wire or suture about the medial ends 41 of the hyoid brace.

Figure 26A:
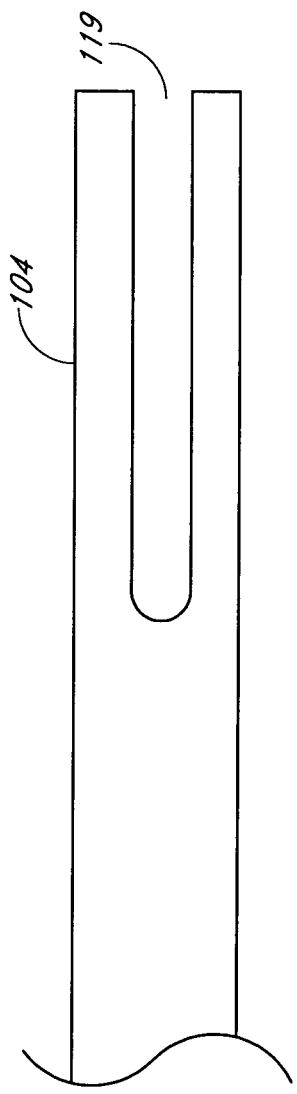
FIG. 26A depicts one embodiment of an outer sheath.
Figure 26B:
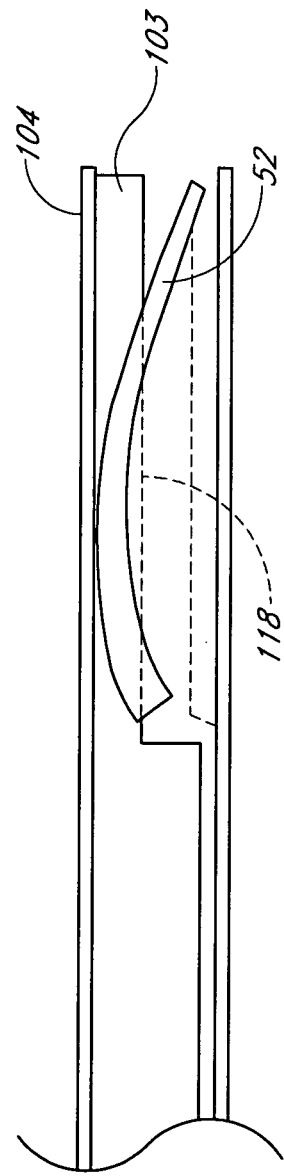
FIG. 26B depicts one embodiment of a distal end of a delivery tool capable of inserting a brace arm next to a hyoid bone in a minimally invasive procedure.

In another embodiment, illustrated in FIGS. 26A and 26B, the delivery member comprises a catheter or insertion tool having a core 101 with a proximal end (not shown) and distal end 103, and an outer sheath 104. The distal end 103 of the core 101 has a surface 118 configured for affixing brace arms 52 to the core 101. The outer sheath 104 is slideable along the length of the core 101 and is capable of encompassing both the core 101 and the brace arms 52. The delivery member is inserted into the dissected area and positioned to release the brace arm 52 at a desired position. The outer sheath 104 is withdrawn to expose the core and release the hyoid brace arm. The core surface 118 is configured to prevent mobility of the brace or parts thereof as the outer sheath is withdrawn, but is configured to allow withdrawal of the core 101 while leaving the brace arm at the dissected site. In one embodiment, the core 101 and outer sheath 104 allow attachment of the brace arms 52 to the hyoid bone or bone segments prior to release of the brace arm 52 in the dissected space. The outer sheath 104 has at least one linear opening 119 along the distal end 106 of the outer sheath 104 to allow sliding of the sheath 104 after the brace arm 52 has been at least partially attached to the hyoid bone 15 or bone segments. In one embodiment, at least one of the linear openings 119 has a shape conformable to a hyoid bone 15 to facilitate alignment of the brace arm 52 with the hyoid bone 15 or bone segments. In one embodiment, the outer sheath 104 is capable of rotation around the core 101. In one embodiment, rotation of the outer sheath 104 exposes the hooks 62 or clips 60 of the brace arm 52. In one embodiment, placing the outer sheath 104 in a retracted position exposes the hooks 62 or clips 60.

In one embodiment, the delivery member 100 has a diameter ranging from about 16 French to about 22 French. In another embodiment, the diameter ranges from about 10 French to about 22 French. In another embodiment, the diameter ranges from about 4 French to about 24 French. In one embodiment, the delivery member has a length of about 6 cm to about 10 cm. In another embodiment, the length is about 6 cm to about 20 cm.

In one embodiment, the outer sheath 104 has palpable markings (not shown) on the core 101 or outer sheath 104 for an clinician to determine the location of the delivery member 100 by tactile sensing. In one embodiment the palpable markings are used by the operator for the placement of puncture access sites lateral to the midline incision site. In one embodiment the delivery member 100 has radiographically visible embedded markers that are visible under fluoroscopy or plain film x-rays. In one embodiment, the outer sheath 104 has a groove (not shown) to facilitate alignment of the delivery member 100 to the hyoid bone 15 or bone segments.

In another embodiment, the delivery member 100 comprises one or more sutures brought through the initial incision site and extending through the dissected area along the hyoid bone 15 and exiting the body through a puncture site lateral to the initial incision site. The sutures may be used to guide the brace components to the intended attachment site and also to attach the brace components to the hyoid bone.

In one embodiment, the delivery member further comprises one or more guidewires inserted into the initial incision site. In one embodiment, the guidewire extends through the dissected area along the hyoid bone and exits the body through a puncture site lateral to the initial incision site. In one embodiment, the core 101 further comprises a guidewire lumen (not shown) running generally from the proximal end to the distal end 103 of the core 101.

In one embodiment, the delivery member 100 has a blunt tip and may also serve as a blunt dissection instrument. Blunt dissection with the delivery member 100 may be performed prior to attachment of the hyoid brace or brace components to the delivery device 100, or concurrently as the brace arm 52 is attached to the hyoid bone.

In one embodiment the manufacturer provides a hyoid brace that is preattached to the delivery device 100. In another embodiment the operator attach the hyoid brace to the delivery device 100 prior to use. In another embodiment the operator selects from a variety of braces with different curvatures and configuration angles and attaches the brace to the delivery device 100.

b. Procedure for Minimally Invasive Insertion

The head of the patient is placed in an extended position to facilitate access to the upper neck, as depicted in FIG. 23A. The skin of the upper neck is sterilized and draped using procedures well known to those with skill in the art. Applying sterile technique and using the thyroid cartilage as a landmark, the hyoid bone is palpated, if possible, and an incision site is identified about the midline of the hyoid bone. In one embodiment, the skin is injected with anesthetic containing epinephrine until anesthesia is achieved. In one embodiment, about a 2 cm incision is made in the skin generally overlying the midportion of the hyoid bone. In one embodiment, the incision is a vertical incision. In another embodiment, the incision is a horizontal incision. The subcutaneous tissue is dissected until the platysma muscle is reached. Skin retractors may used to maximize and maintain the visibility of the exposed incision site. At least a 1 cm vertical midline incision is made in the platysma muscle to expose at least a portion of the hyoid bone. Blunt dissection is then performed along the hyoid bone to each lateral side of the incision site to created a dissected space and to facilitate insertion of a hyoid brace along the anterior surface of the hyoid bone. In one embodiment, blunt dissection is initiated by curved surgical forceps. In another embodiment, blunt dissection is performed by a curved blunt dissection instrument having a curvature portion that generally approximates the curvature of the hyoid bone from the midline to at least the lesser horn, or more. In one embodiment, hemostasis of the incision and dissection area is achieved using an electrocautery device known to those skilled in the art.

In one embodiment the blunt dissection instrument is used to measure the size and configuration of the hyoid bone. In another embodiment, the blunt dissection instrument further comprises a distal end with an imaging sensor. In one embodiment the size and configuration information may be used to select a particular brace appropriate to particular characteristics of the hyoid bone to be treated. In another embodiment the blunt dissection instrument is palpable through the skin to allow the operator to determine the extent of dissection and to allow the operator place puncture sites lateral to the initial incision site to facilitate manipulation of instruments and an attachment of a brace onto the hyoid bone.

In one embodiment, the hyoid brace is inserted into the dissection space and approximately against the surface of the hyoid bone 15. In one embodiment, the placement of the hyoid brace or brace components are performed under ultrasound guidance. In one embodiment, the placement of the hyoid brace or brace components is performed under fluoroscopy. In one embodiment, a hyoid brace in the folded position is inserted through an incision site. After or during the insertion, the hyoid brace then assumes the unfolded position in approximation along the hyoid bone 15.

In one embodiment, the hyoid brace is inserted manually by hand into the dissected area. In another embodiment, the hyoid brace is inserted into the dissected area using a delivery member 100.

In another embodiment, brace arms 52 are inserted separately into the dissected space and attached to the hyoid bone 15. A bridge 53 is then attached to each brace arm 52 and adjusted, if possible, to position the brace arms 52. The delivery member releases the brace or brace arms.

In another embodiment, the brace arms are inserted into the infrahyoid or suprahyoid musculature adjacent to the hyoid bone. Attachment of the bridge reconfigures the soft tissue about the hyoid bone and dilates or supports the pharyngeal walls, depending upon the internal bias and flexibility of the brace arms and bridge.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method of treating a patient, comprising the steps of:
providing a hyoid bone support, the support having a first arm and a second arm which are transformable from a moveable relationship with respect to each other to a fixed relationship with respect to each other, wherein the two arms are connected to one another;
attaching the first arm to a first part of a hyoid bone;
attaching the second arm to a second part of the hyoid bone;
changing the configuration of the hyoid bone by moving the two arms while in the moveable relationship with respect to each other; and
securing the support by placing the two arms in the fixed relationship with respect to each other.

2. A method of treating a patient as in claim 1, wherein the changing the configuration step further comprises increasing a lateral distance between the first and second parts of the hyoid bone.

3. A method of treating a patient as in claim 1, wherein the changing the configuration step further comprises increasing an anterior-posterior distance between the first and second parts of the hyoid bone.

4. A method of treating a patient as in claim 3, wherein the increasing the anterior-posterior distance of the changing the configuration step further comprises inserting at least one spacer between the first and second parts of the hyoid bone.

5. A method of treating a patient as in claim 3, wherein the increasing the anterior-posterior distance of the changing the configuration step further comprises attaching a brace to the first and second arms of the hyoid bone support to expand the distance between the first and second arms of the hyoid bone support.

6. A method of treating a patient as in claim 1, wherein the changing the configuration step is accomplished before at least one of the attaching steps.

7. A method of treating a patient as in claim 1, wherein the changing the configuration step is accomplished following both of the attaching steps.

8. A method of treating a patient as in claim 1, wherein at least one of the attaching steps further comprises using a bone screw.

9. A method of treating a patient as in claim 1, wherein at least one of the attaching steps further comprises using a bone clip.

10. A method of treating a patient as in claim 1, wherein at least one of the attaching steps further comprises using a suture.

11. A method of treating a patient as in claim 1, wherein at least one of the attaching steps further comprises using an adhesive.

12. A method of treating a patient as in claim 1, wherein at least one of the attaching steps further comprises using a mechanical interfit between the hyoid bone and the hyoid bone support.

* * * * *